(12) United States Patent
O'Harte et al.

(10) Patent No.: US 10,118,954 B2
(45) Date of Patent: Nov. 6, 2018

(54) APELIN ANALOGUES

(71) Applicant: University of Ulster, Coleraine, Londonderry (GB)

(72) Inventors: Finbarr Paul Mary O'Harte, Portstewart (GB); Peter Raymond Flatt, Portstewart (GB)

(73) Assignee: Univeristy of Ulster, Londonderry (IE)

( * ) Notice: Subject to any disclaimer, the term of this patent is extended or adjusted under 35 U.S.C. 154(b) by 0 days.

(21) Appl. No.: 15/307,248

(22) PCT Filed: Apr. 29, 2015

(86) PCT No.: PCT/EP2015/059288
§ 371 (c)(1),
(2) Date: Oct. 27, 2016

(87) PCT Pub. No.: WO2015/165936
PCT Pub. Date: Nov. 5, 2015

(65) Prior Publication Data
US 2017/0066810 A1    Mar. 9, 2017

(30) Foreign Application Priority Data

Apr. 29, 2014 (GB) .................................. 1407532.9

(51) Int. Cl.
*A61K 38/00* (2006.01)
*C07K 14/52* (2006.01)
*C07K 14/575* (2006.01)

(52) U.S. Cl.
CPC ............ *C07K 14/575* (2013.01); *C07K 14/52* (2013.01); *A61K 38/00* (2013.01)

(58) Field of Classification Search
CPC ....... A61K 38/00; C07K 14/52; C07K 14/575
USPC .......................... 530/300, 324, 325, 326, 327
See application file for complete search history.

(56) References Cited

U.S. PATENT DOCUMENTS

| 7,635,751 B2 * | 12/2009 | Kitada | C07K 14/47 530/300 |
| 2013/0096050 A1 * | 4/2013 | Shandler | A61K 38/2278 514/1.7 |
| 2013/0196899 A1 | 8/2013 | Zecri et al. | |
| 2014/0275489 A1 * | 9/2014 | Stevis | C07K 14/47 530/387.3 |

FOREIGN PATENT DOCUMENTS

WO    03063892 A1    8/2003

OTHER PUBLICATIONS

Alexandre Murza et al., Elucidation of the Structure-Activity Relationships of Apelin: Influence of Unnatural Amino Acids on Binding, Signaling, and Plasma Stability, CHEMMEDCHEM, vol. 7, No. 2, Feb. 6, 2012, pp. 318-325, XP055072892.
Dennis K. Lee et al., Modification of the Terminal Residue of Apelin-13 Antagonizes Its Hypotensive Action, Endocrinology, vol. 146, No. 1, Jan. 2005, pp. 231-236, XP-002741939.
Oleg I. Pisarenko et al., Effects of structural analogues of apelin-12 in acute myocardial infarction in rats, Journal of Pharmacology & Pharmacotherapeutics, Jul. 2013, vol. 4, Issue 3, pp. 198-203, XP-002741940.
International Search Report and Written Opinion dated Jul. 22, 2015, for corresponding International Application No. PCT/EP2015/059288; International Filing Date: Apr. 29, 2015 consisting of 13-pages.

* cited by examiner

*Primary Examiner* — Julie Ha
(74) *Attorney, Agent, or Firm* — Christopher & Weisberg, P.A.

(57) ABSTRACT

A pharmaceutical composition with a peptide analog of apelin, and a method of treatment for various conditions are described. An exemplary embodiment is a peptide analog comprising at least residues 2-13 of SEQ ID NO: 1 and further comprising at least a substitution or modification at residue 13 of SEQ ID NO: 1. A pharmaceutical composition comprising the peptide analog of the present invention and method of treatment for diabetes, stimulating insulin release, and moderating blood glucose excursions by administering the peptide analog of the present invention to a patient in need thereof are described.

14 Claims, 29 Drawing Sheets

Specification includes a Sequence Listing.

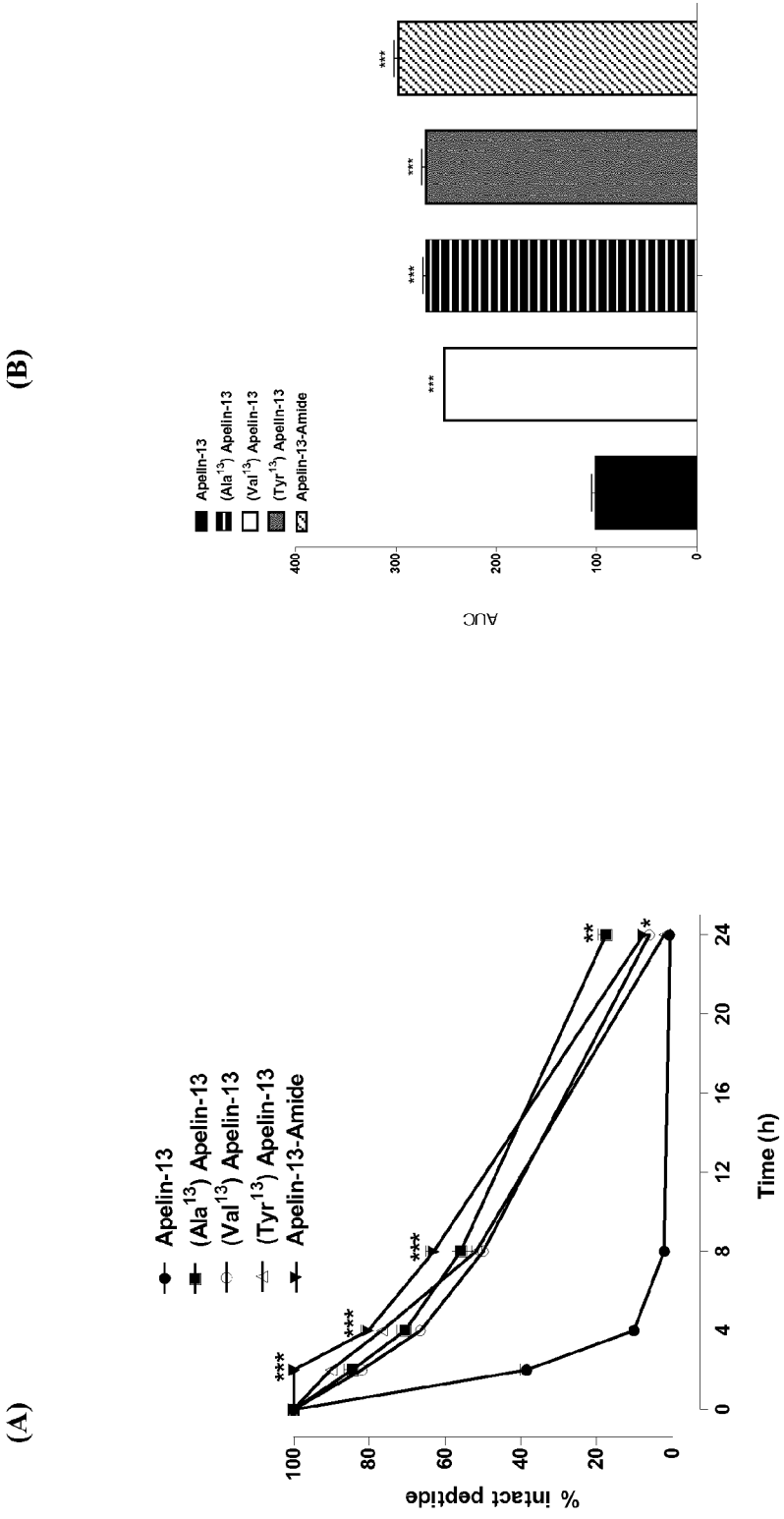
Fig. 1 Stability of various apelin-13 related analogues after incubation with pooled plasma from fasted normal mice.

Fig. 2 Sequence of various apelin-13 analogues showing potential enzymatic cleavage points.

*Apelin-13*

Gln-Arg-Pro-Arg-Leu-Ser-His-Lys-Gly-Pro-Met ↓ Pro ↓ Phe    (SEQ ID NO:1)

*(Ala$^{13}$)apelin-13*

Gln-Arg-Pro-Arg-Leu-Ser-His-Lys ↓ Gly-Pro-Met ↓ Pro-Ala    (SEQ ID NO:2)

*(Val$^{13}$)apelin-13*

Gln-Arg-Pro-Arg-Leu-Ser-His-Lys-Gly-Pro-Met-Pro ↓ Val    (SEQ ID NO:3)

*(Tyr$^{13}$)apelin-13*

Gln-Arg-Pro-Arg-Leu-Ser-His ↓ Lys-Gly-Pro-Met-Pro ↓ Tyr    (SEQ ID NO:4)

*Apelin-13-amide*

Gln-Arg-Pro-Arg-Leu-Ser-His-Lys-Gly-Pro-Met-Pro ↓ Phe —Amide (SEQ ID NO:5)

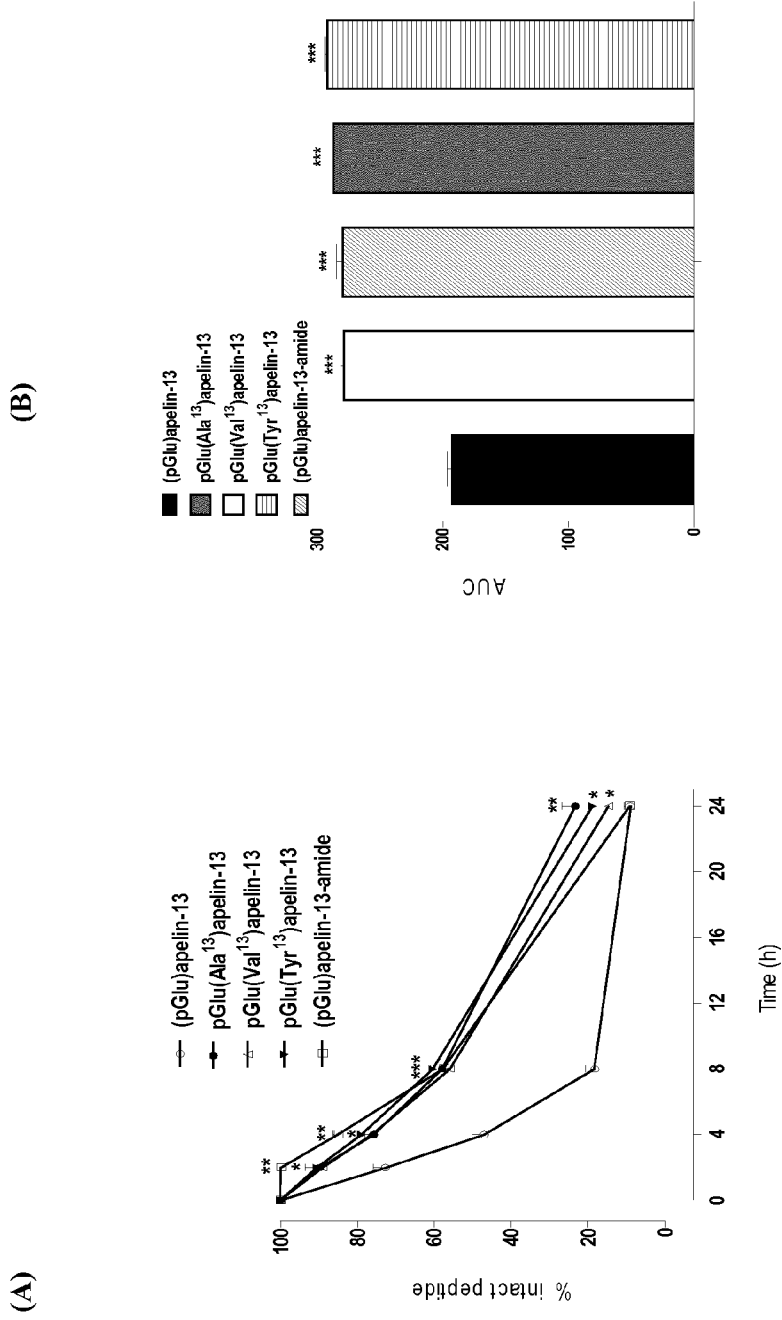
Fig. 3 Stability of various (pGlu)-apelin-13 related analogues after incubation with fasting normal mouse plasma.

Fig. 4 Sequence of various (pGlu)apelin-13 analogues showing potential degradation cleavage points.

*(pGlu)apelin-13* pGlu-Arg-Pro-Arg-Leu ↓ Ser ↓ His-Lys-Gly-Pro-Met-Pro ↓ Phe    (SEQ ID NO:6)

*pGlu(Ala$^{13}$)apelin-13* pGlu-Arg-Pro-Arg-Leu-Ser ↓ His-Lys-Gly-Pro-Met-Pro-Ala    (SEQ ID NO:7)

*pGlu(Val$^{13}$)apelin-13* pGlu-Arg-Pro-Arg-Leu ↓ Ser-His-Lys-Gly-Pro-Met-Pro ↓ Val    (SEQ ID NO:8)

*pGlu(Tyr$^{13}$)apelin-13* pGlu-Arg-Pro-Arg-Leu ↓ Ser ↓ His-Lys-Gly-Pro-Met-Pro ↓ Tyr    (SEQ ID NO:9)

*(pGlu)apelin-13-amide* pGlu-Arg-Pro-Arg-Leu ↓ Ser-His-Lys-Gly-Pro-Met-Pro ↓ Phe —Amide    (SEQ ID NO:10)

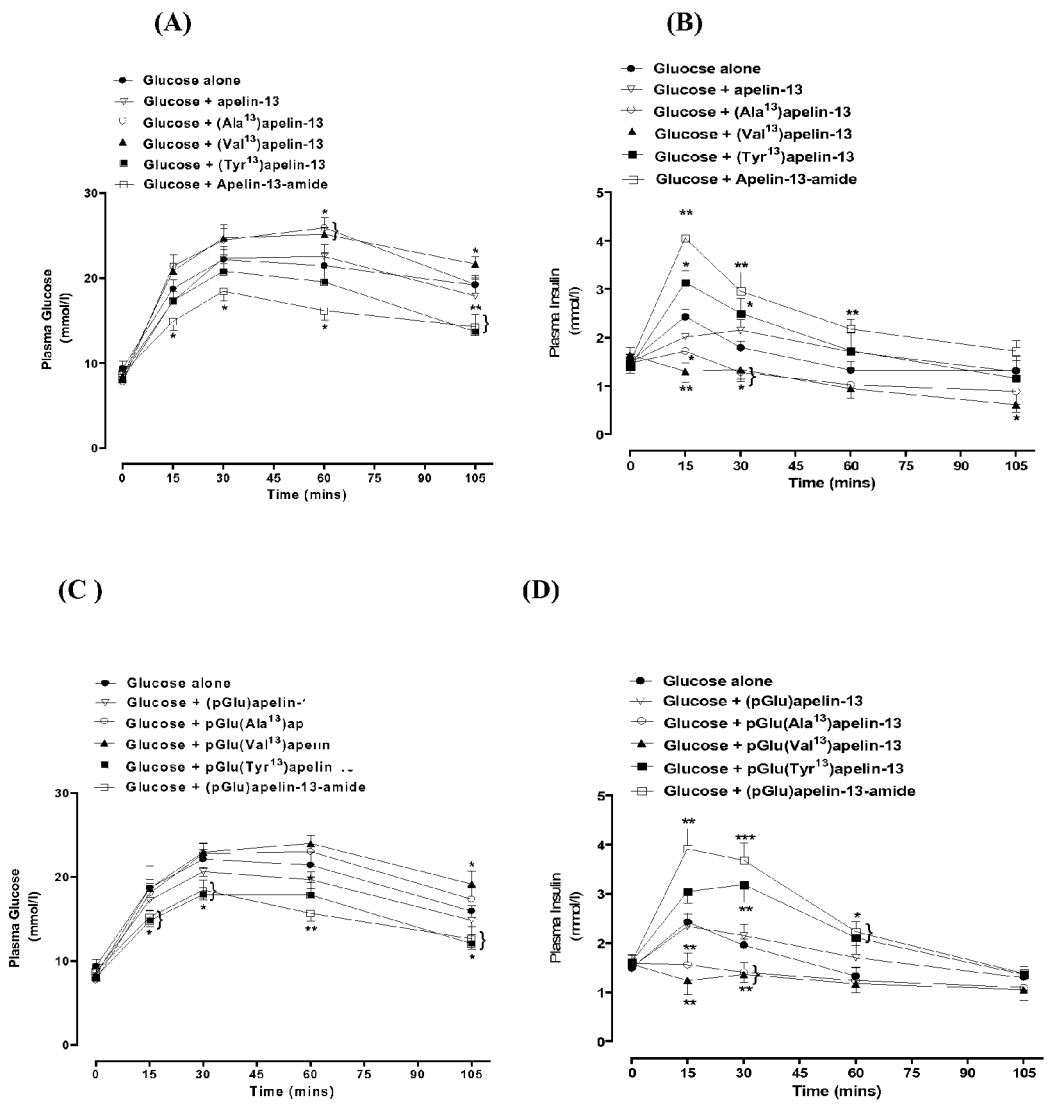
Fig. 5 Acute effects of various apelin-13 (A & B) and pGlu apelin-13 (C & D) related analogues on blood glucose and plasma insulin secretion in high-fat fed NIH Swiss mice.

Fig. 6 Acute effects of (Tyr$^{13}$)apelin-13 and the antagonistic properties of (Ala$^{13}$)apelin-13, alone and in combination, on blood glucose and plasma insulin secretion in high-fat fed NIH Swiss mice.

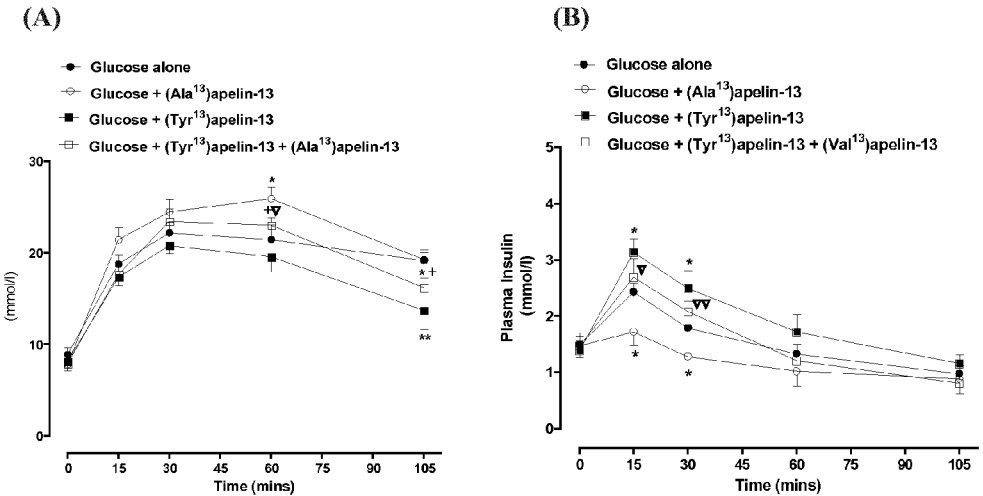

Fig. 7 Acute effects of (Tyr$^{13}$)apelin-13 and the antagonistic properties of (Val$^{13}$)apelin-13, alone and in combination, on blood glucose and plasma insulin secretion in high-fat fed NIH Swiss mice.

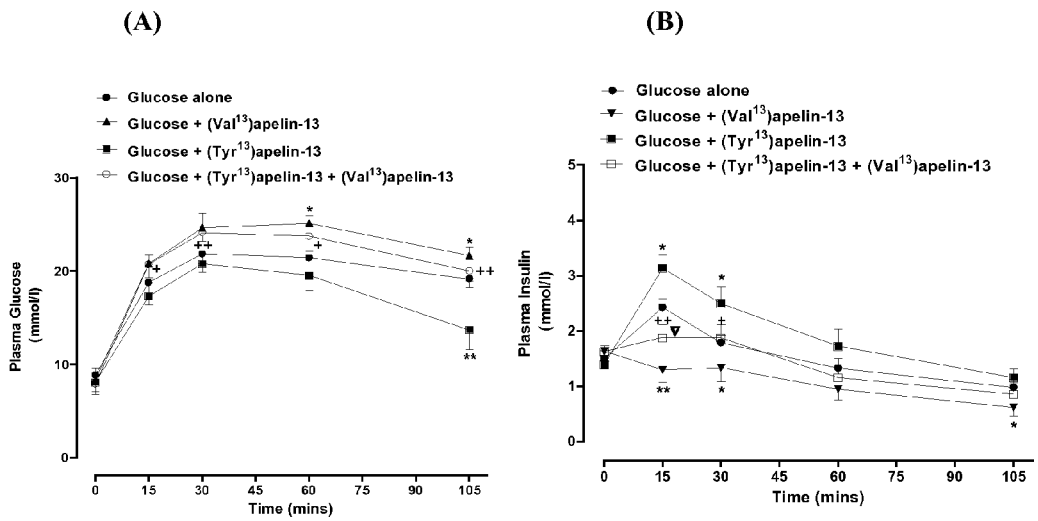

Fig. 8 Acute effects of Apelin-13-amide and the antagonistic properties of (Ala$^{13}$)apelin-13, alone and in combination, on blood glucose and plasma insulin secretion in high-fat fed NIH Swiss mice.

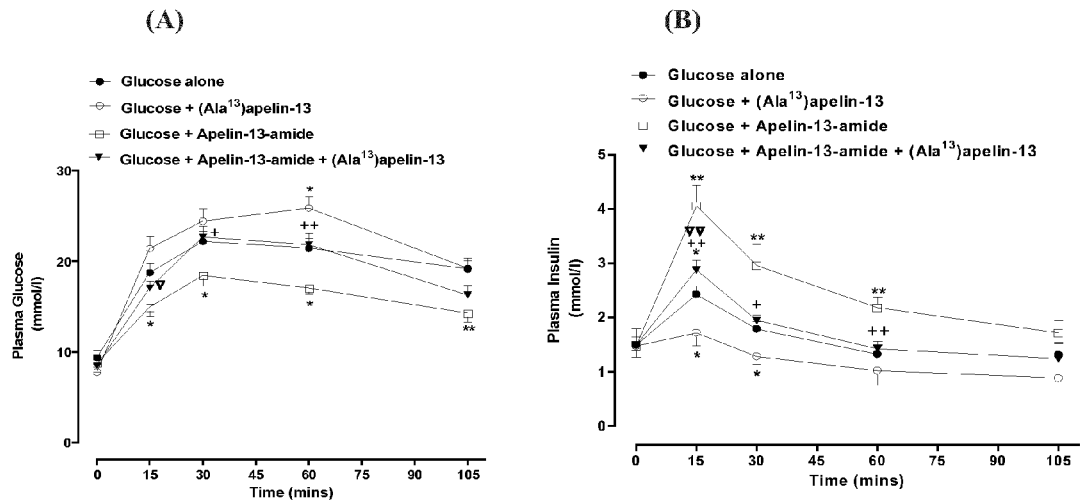

Fig. 9 Acute effects of Apelin-13-amide and the antagonistic properties of (Val$^{13}$)apelin-13, alone and in combination, on blood glucose and plasma insulin secretion in high-fat fed NIH Swiss mice.

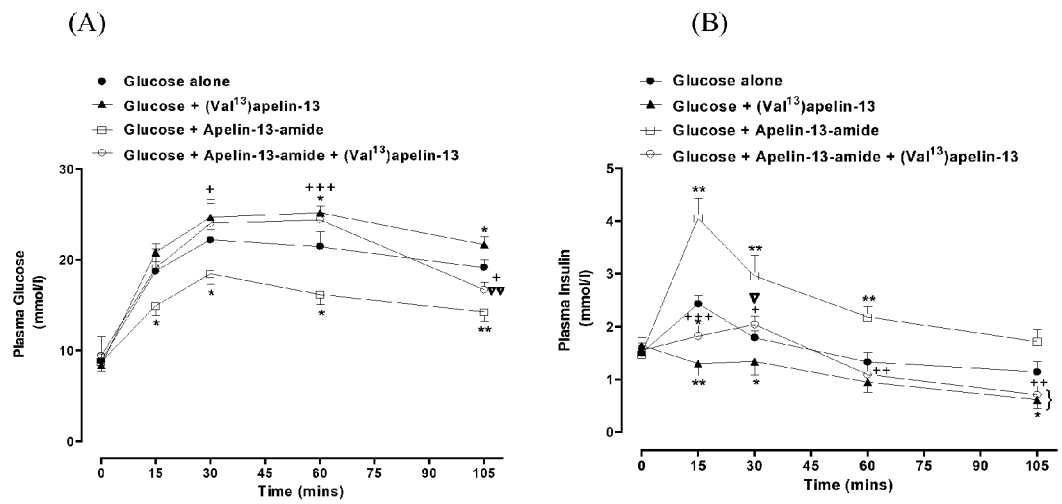

Fig. 10 Duration of biological action of various apelin related analogues on glucose-lowering and plasma insulin secretion in high-fat fed NIH Swiss mice following a 2 h delay.
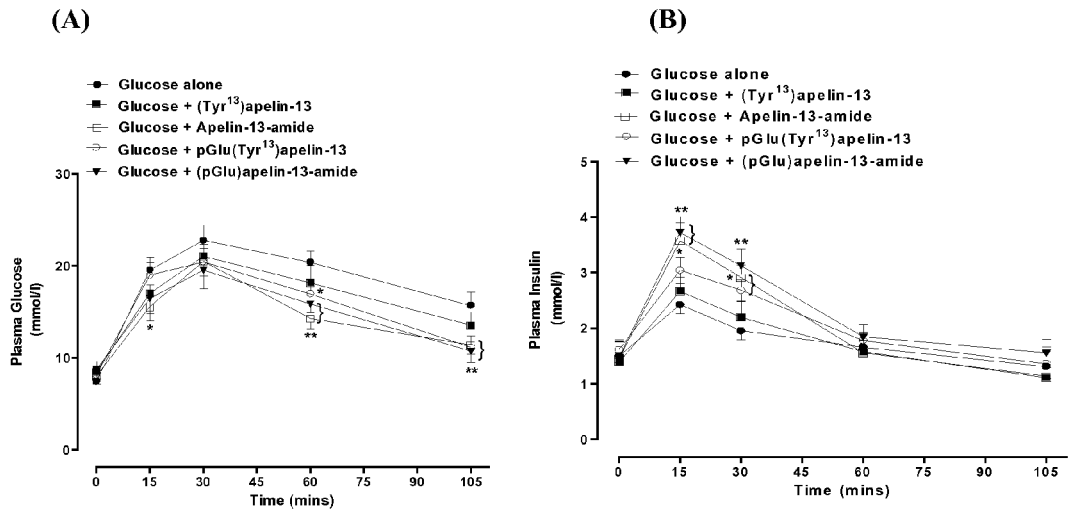
Fig. 11 Duration of biological action of various apelin related analogues on glucose-lowering and plasma insulin secretion in high-fat fed NIH Swiss mice following an 8 h delay.
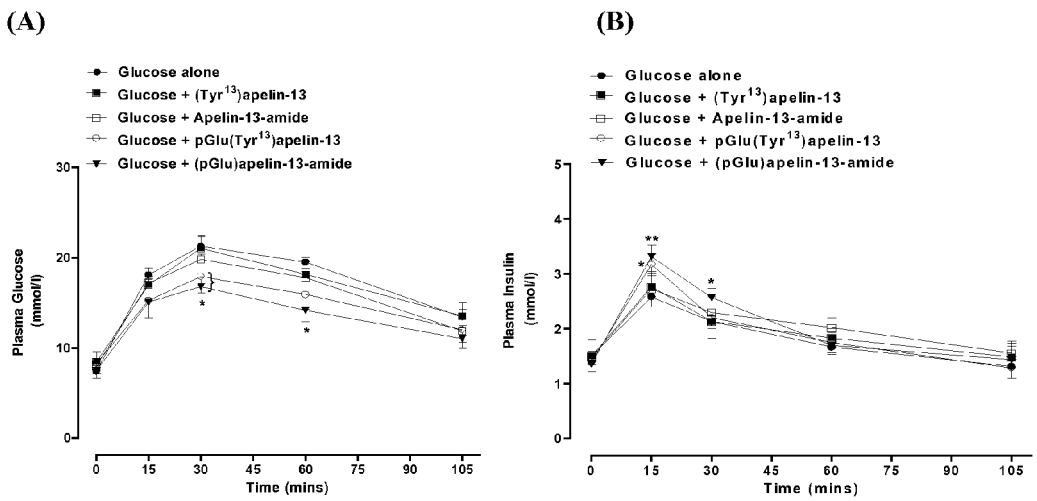

Fig. 12 Acute effects of fatty acid derived apelin analogues on blood glucose and plasma insulin secretion in high-fat fed NIH Swiss mice.
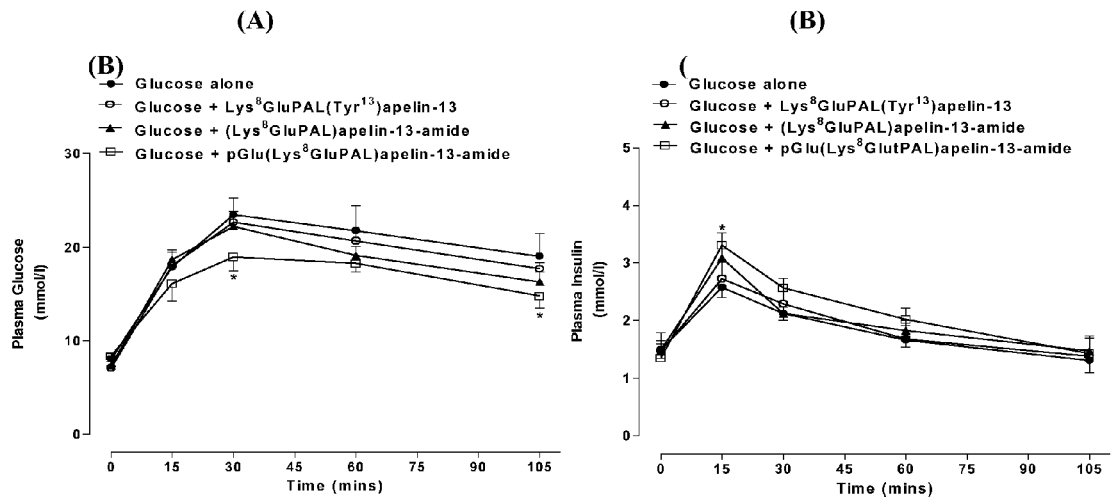
Fig. 13 Duration of biological action of fatty acid derived apelin analogues on glucose-lowering and plasma insulin secretion in high-fat fed NIH Swiss mice following a 16 h delay.
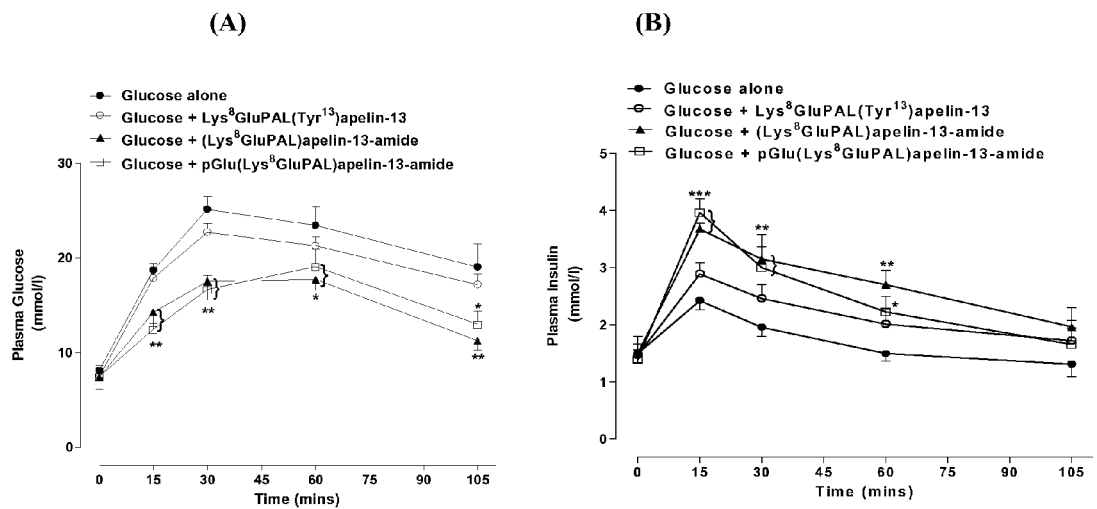

Fig. 14 Chronic 28 day study showing the effects of twice daily administration of exendin-4(1-39), apelin-13-amide and (pGlu)apelin-13-amide on (A) bodyweight and (B) bodyweight change (%) in high-fat fed NIH Swiss mice.

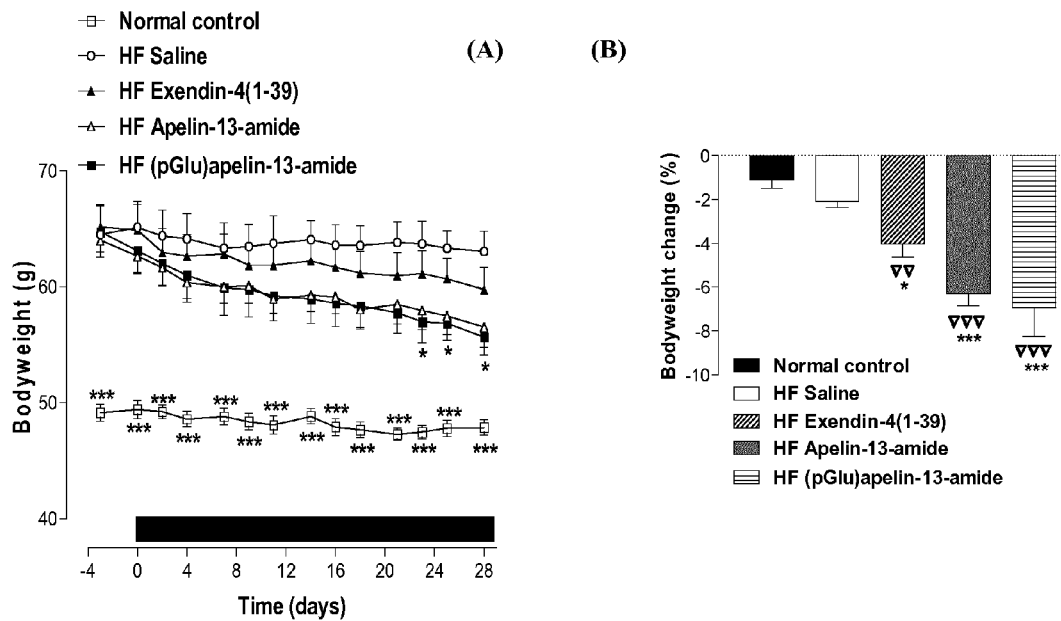

Fig. 15 Chronic 28 day study showing effects of twice daily administration of exendin-4(1-39), apelin-13-amide and (pGlu)apelin-13-amide on (A) cumulative food intake and (B) energy intake in high-fat fed NIH Swiss mice.

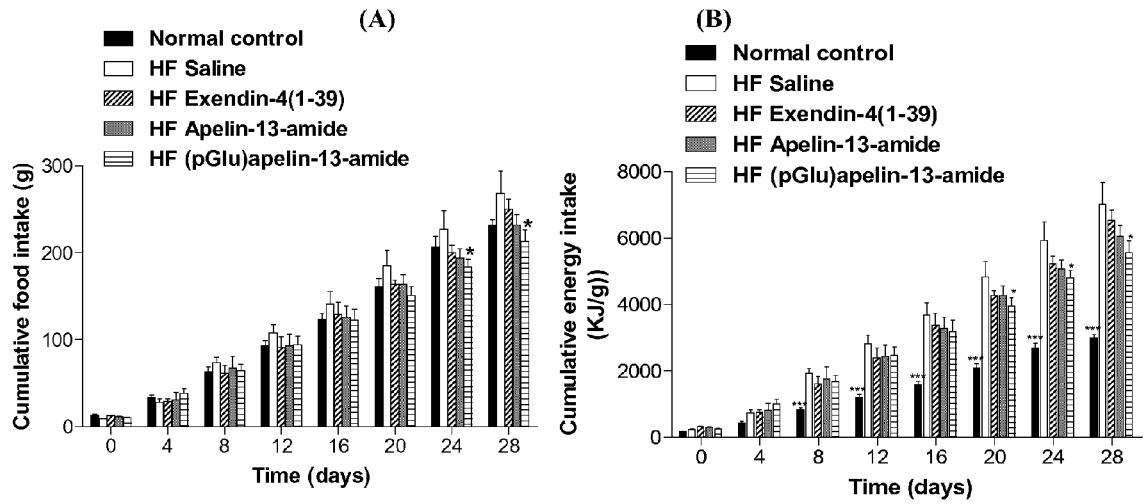

Fig. 16 Chronic 28 day study showing effects of twice daily administration of exendin-4(1-39), apelin-13-amide and (pGlu)apelin-13-amide on (A) non-fasting blood glucose and (B) plasma insulin in high-fat fed NIH Swiss mice.

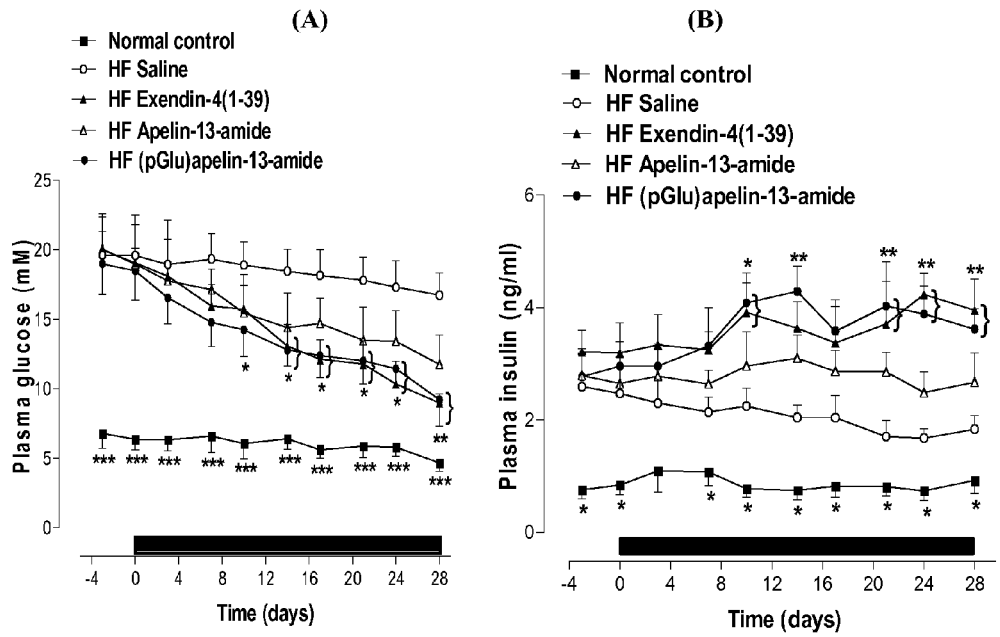

Fig. 17 Chronic 28 day study showing effects of twice daily administration of exendin-4(1-39), apelin-13-amide and (pGlu)apelin-13-amide on (A) blood glucose and (B) plasma insulin in response to an i.p. glucose challenge in high-fat fed NIH Swiss mice.

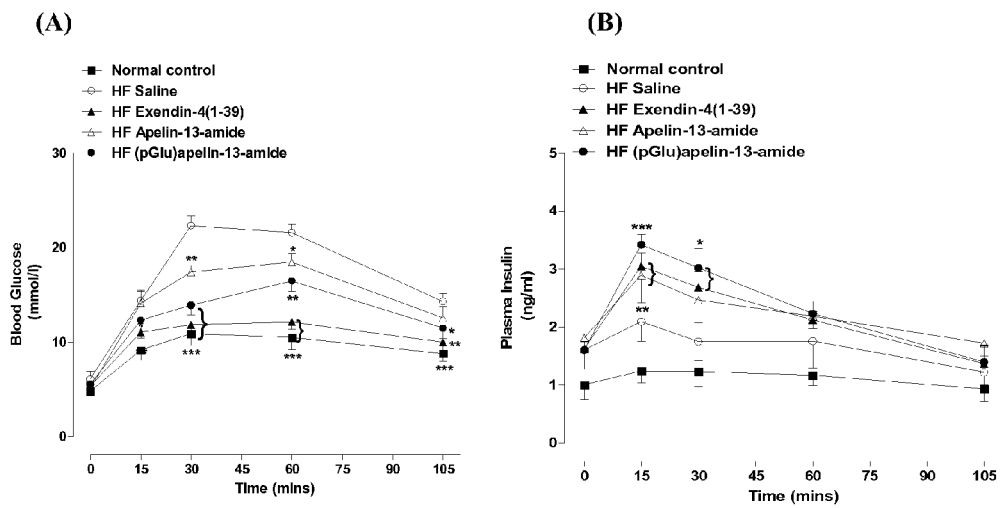

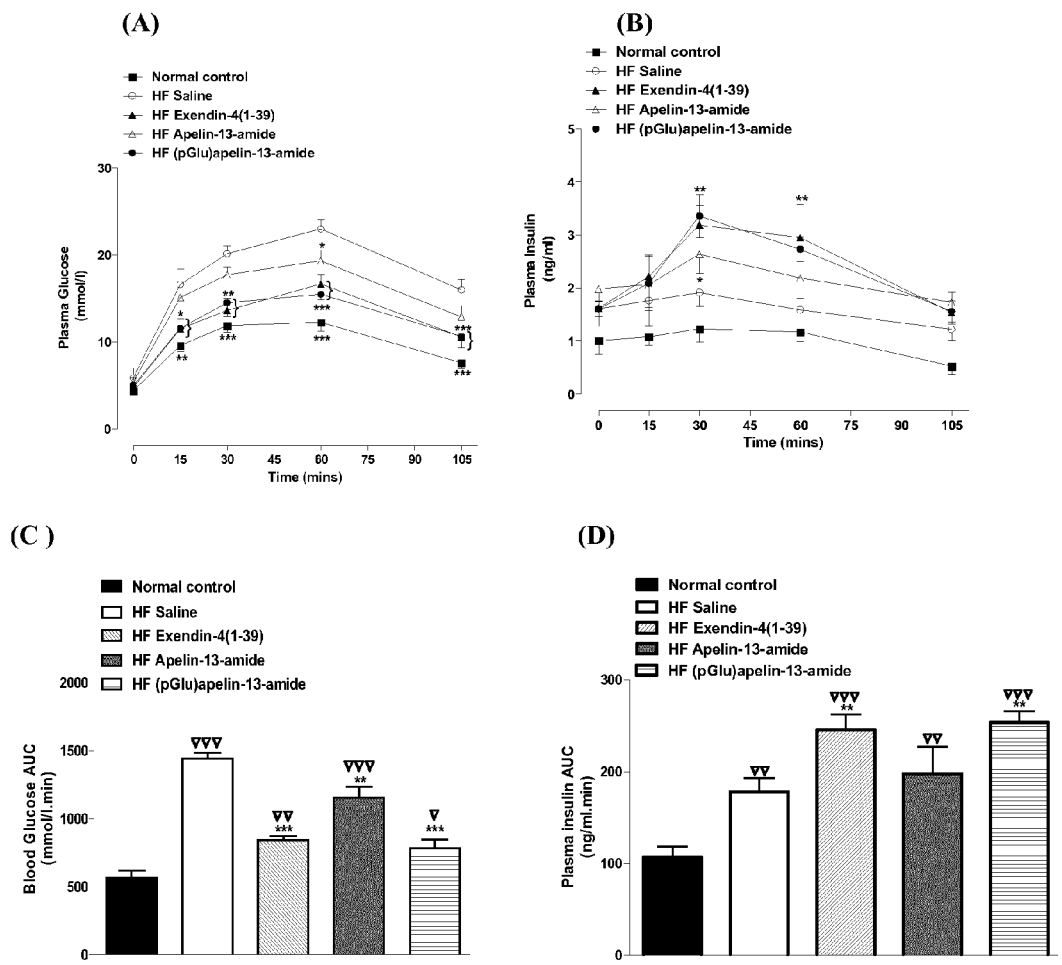
Fig. 18 Chronic 28 day study showing effects of twice daily administration of exendin-4(1-39), apelin-13-amide and (pGlu)apelin-13-amide on (A) blood glucose and (B) plasma insulin in response to an oral glucose challenge in high-fat fed NIH Swiss mice.

Fig. 19 Chronic 28 day study showing effects of twice daily administration of exendin-4(1-39), apelin-13-amide and (pGlu)apelin-13-amide on (A) blood glucose and (B) plasma insulin in response to feeding in high-fat fed NIH Swiss mice.
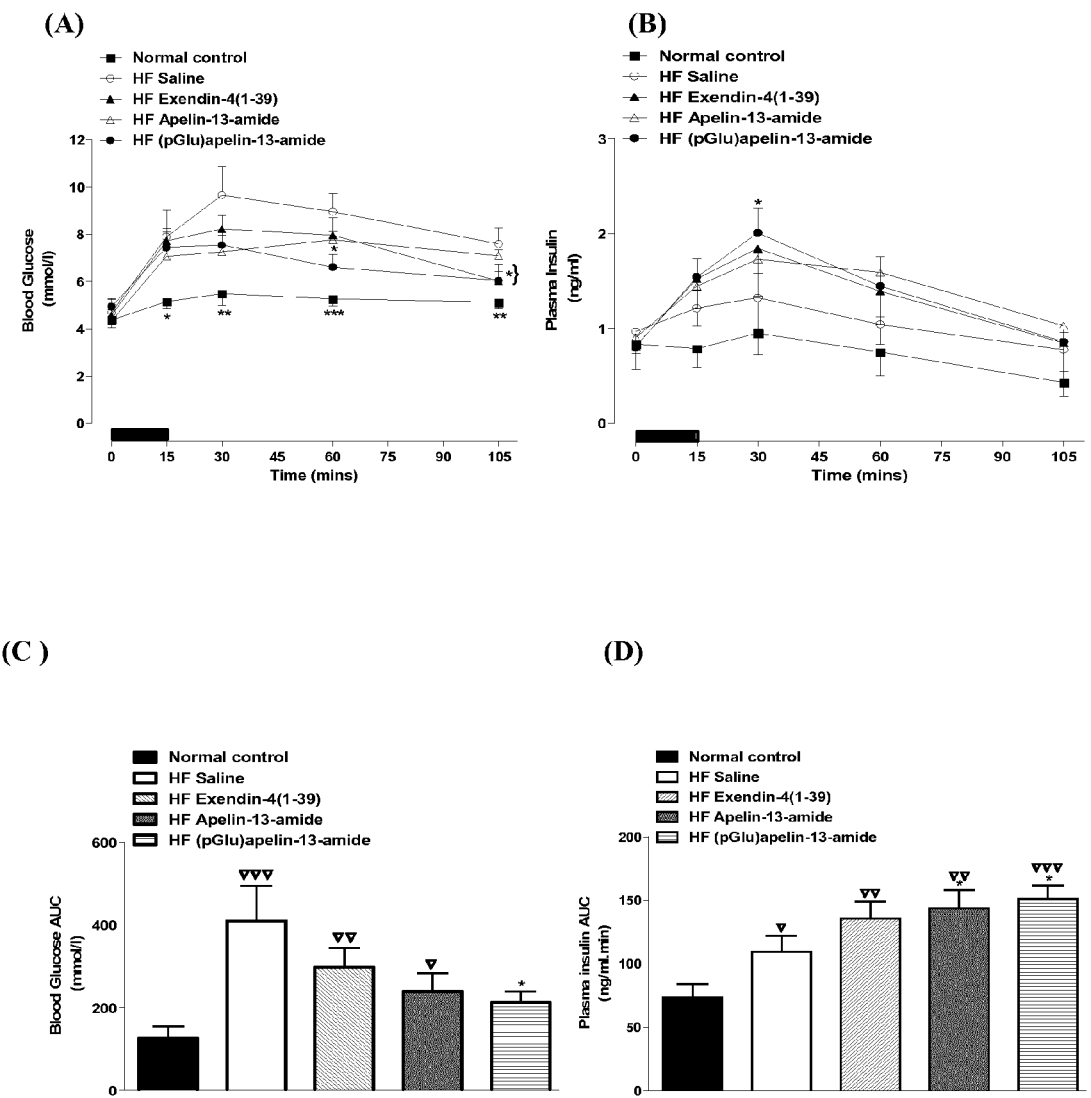

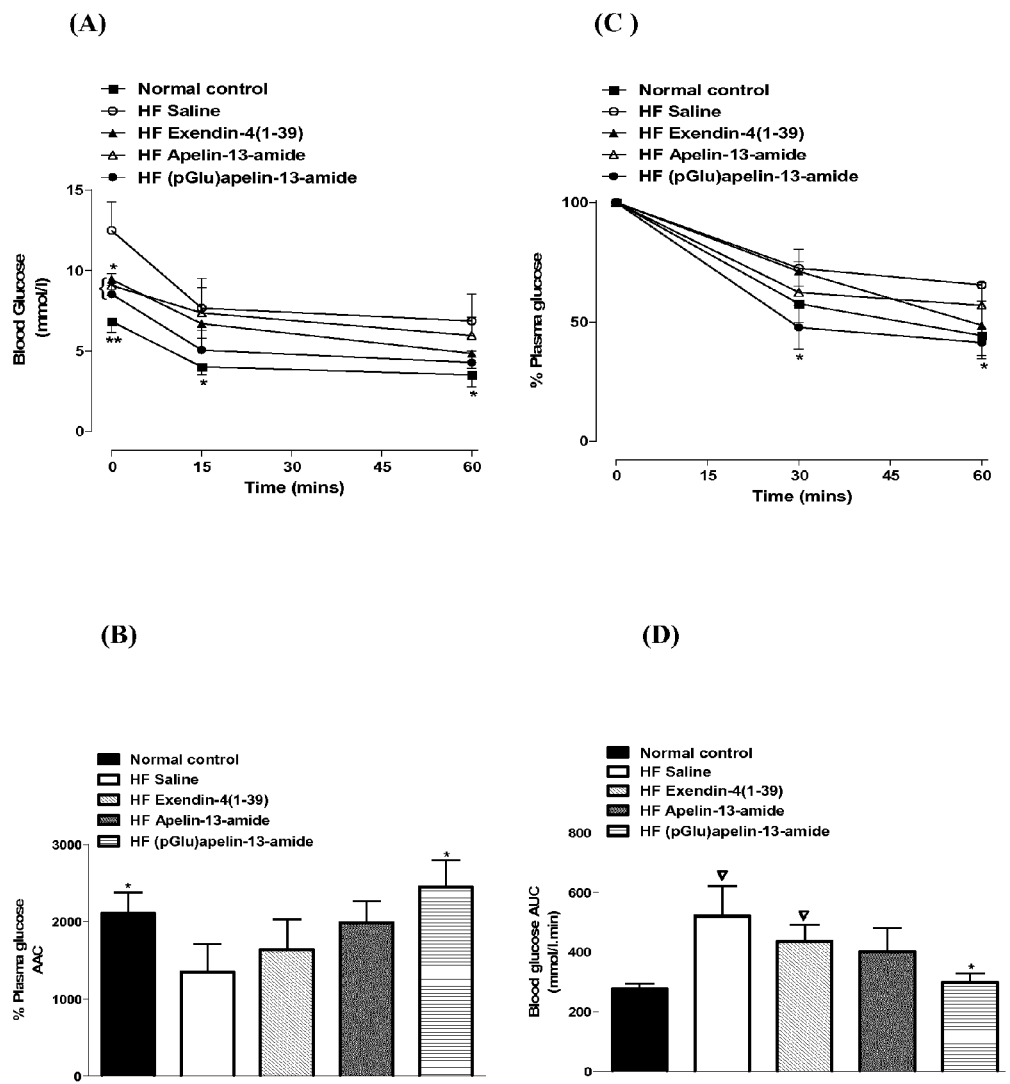
Fig. 20 Chronic 28 day study showing effects of twice daily administration of exendin-4(1-39), apelin-13-amide and (pGlu)apelin-13-amide on blood glucose in response to insulin sensitivity in high-fat fed NIH Swiss mice.

Fig. 21 Chronic 28 day study showing effects of twice daily administration of exendin-4(1-39), apelin-13-amide and (pGlu)apelin-13-amide on glycated haemoglobin (HbA$_{1c}$) in high-fat fed NIH Swiss mice.

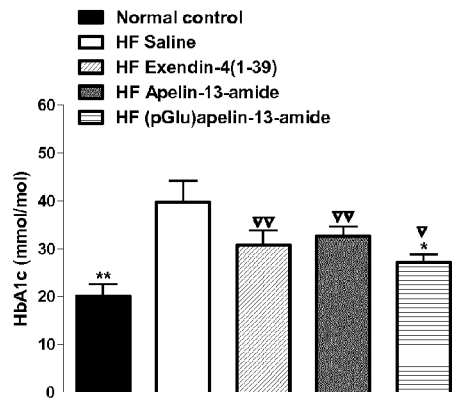

Fig. 22 Chronic 28 day study showing effects of twice daily administration of exendin-4(1-39), apelin-13-amide and (pGlu)apelin-13-amide on (A) bodyweight and (B) percentage fat mass as measured by DEXA scanning in high-fat fed NIH Swiss mice.

(A)

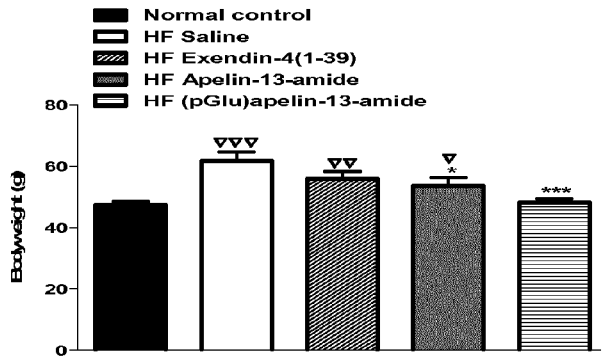

(B)

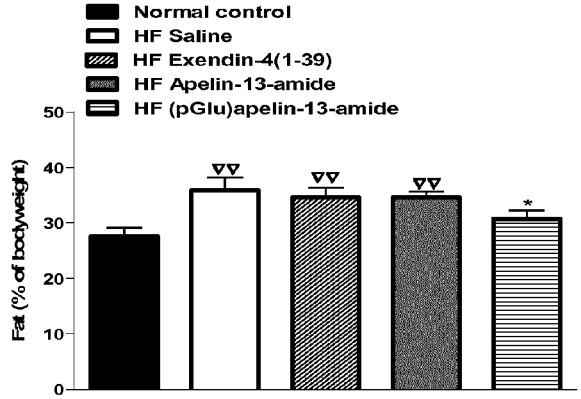

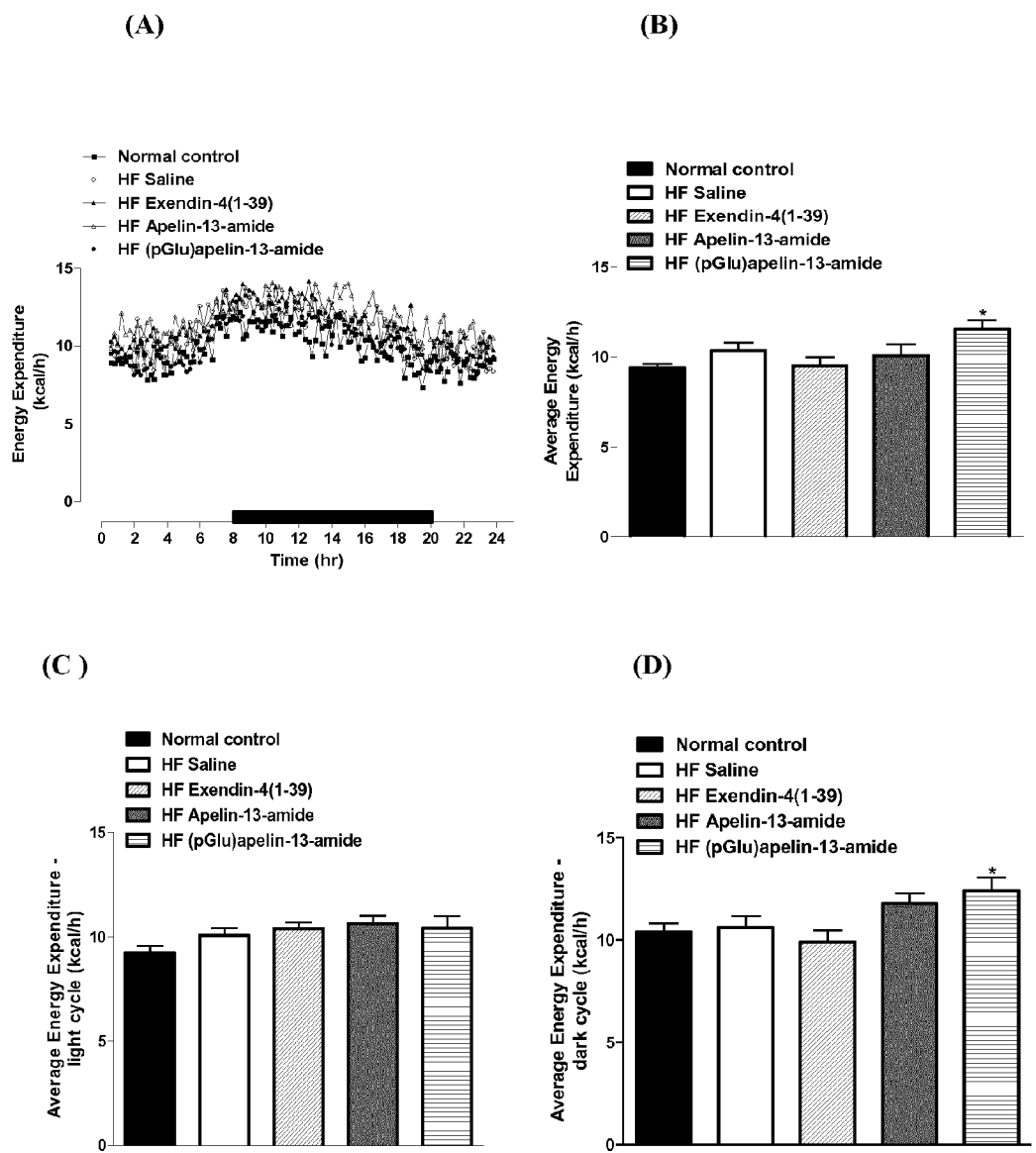
Fig. 23 Chronic 28 day study showing effects of twice daily administration of exendin-4(1-39), apelin-13-amide and (pGlu)apelin-13-amide on energy expenditure in high-fat fed NIH Swiss mice.

Fig. 24 Chronic 28 day study showing effects of once daily administration of liraglutide, (Lys$^8$gluPAL)apelin-13-amide and pGlu(Lys$^8$gluPAL)apelin-13-amide on (A) bodyweight and (B) bodyweight change (%) in high-fat fed NIH Swiss mice.
(A)
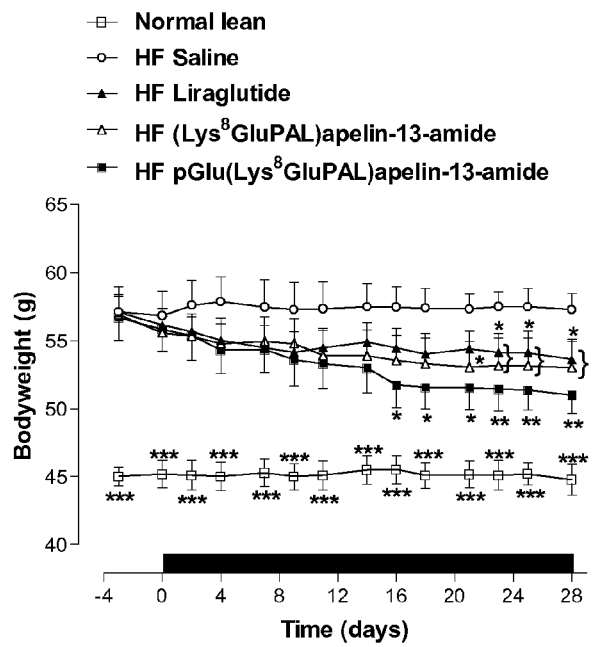
(B)
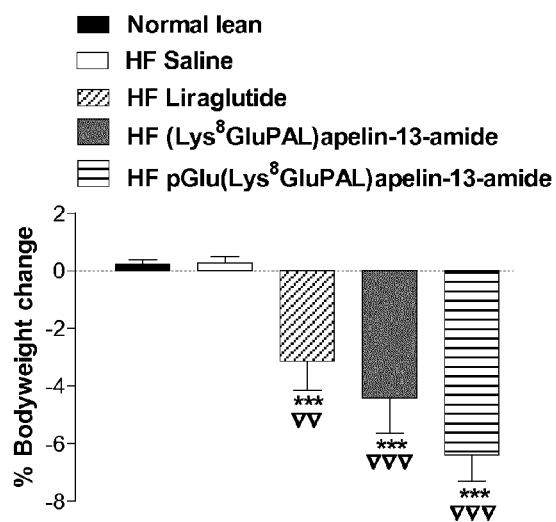

Fig. 25 Chronic 28 day study showing effects of once daily administration of liraglutide, (Lys$^8$gluPAL)apelin-13-amide and pGlu(Lys$^8$gluPAL)apelin-13-amide on (A) cumulative food intake and (B) energy intake in high-fat fed NIH Swiss mice.
(A)
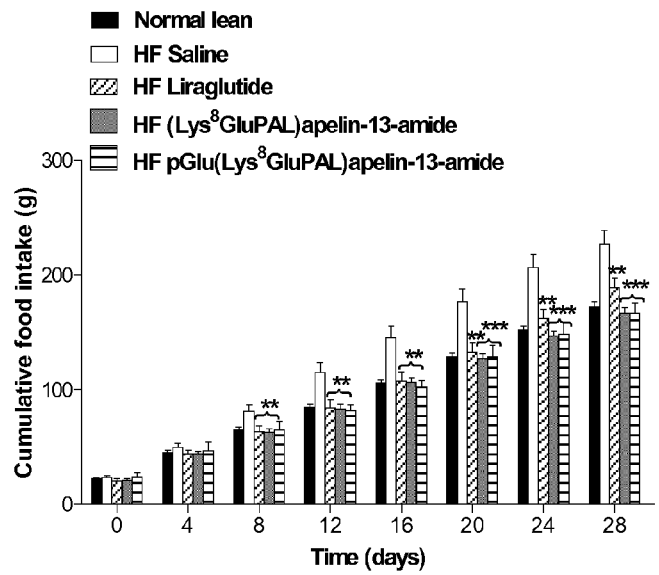
(B)
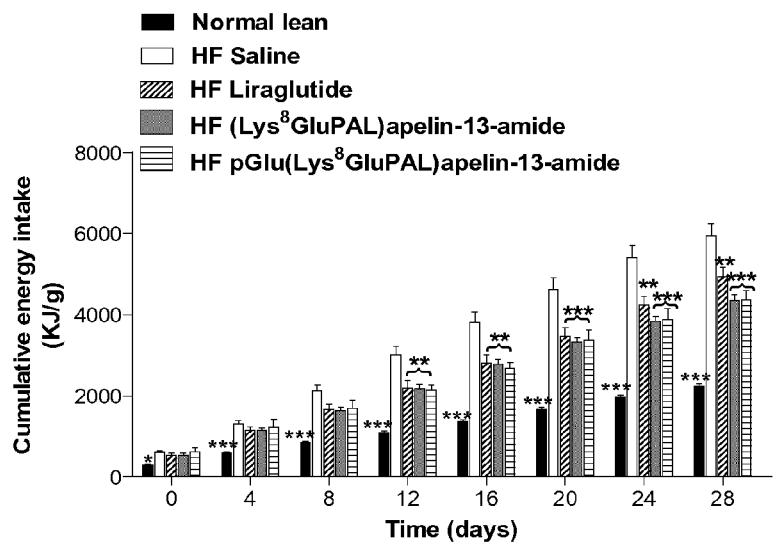

Fig. 26 Chronic 28 day study showing effects of once daily administration of liraglutide, (Lys$^8$gluPAL)apelin-13-amide and pGlu(Lys$^8$gluPAL)apelin-13-amide on (A) non-fasting blood glucose and (B) plasma insulin in high-fat fed NIH Swiss mice.
(A)
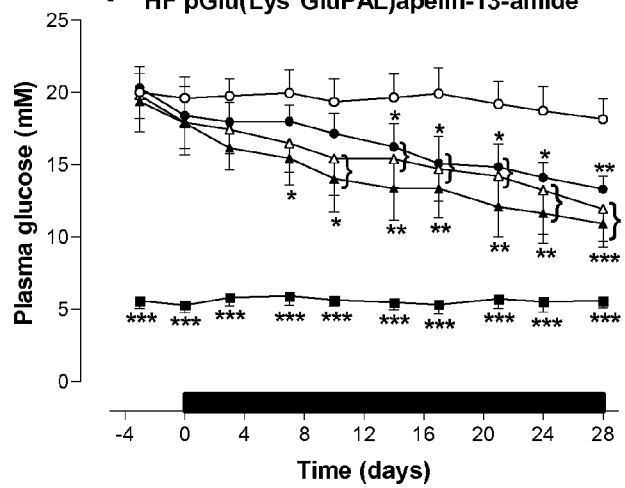
(B)
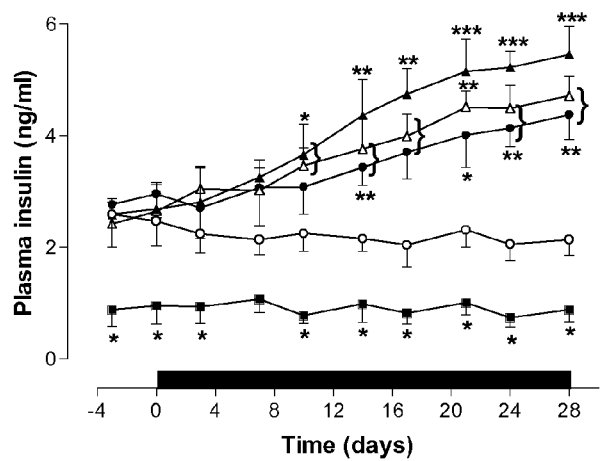

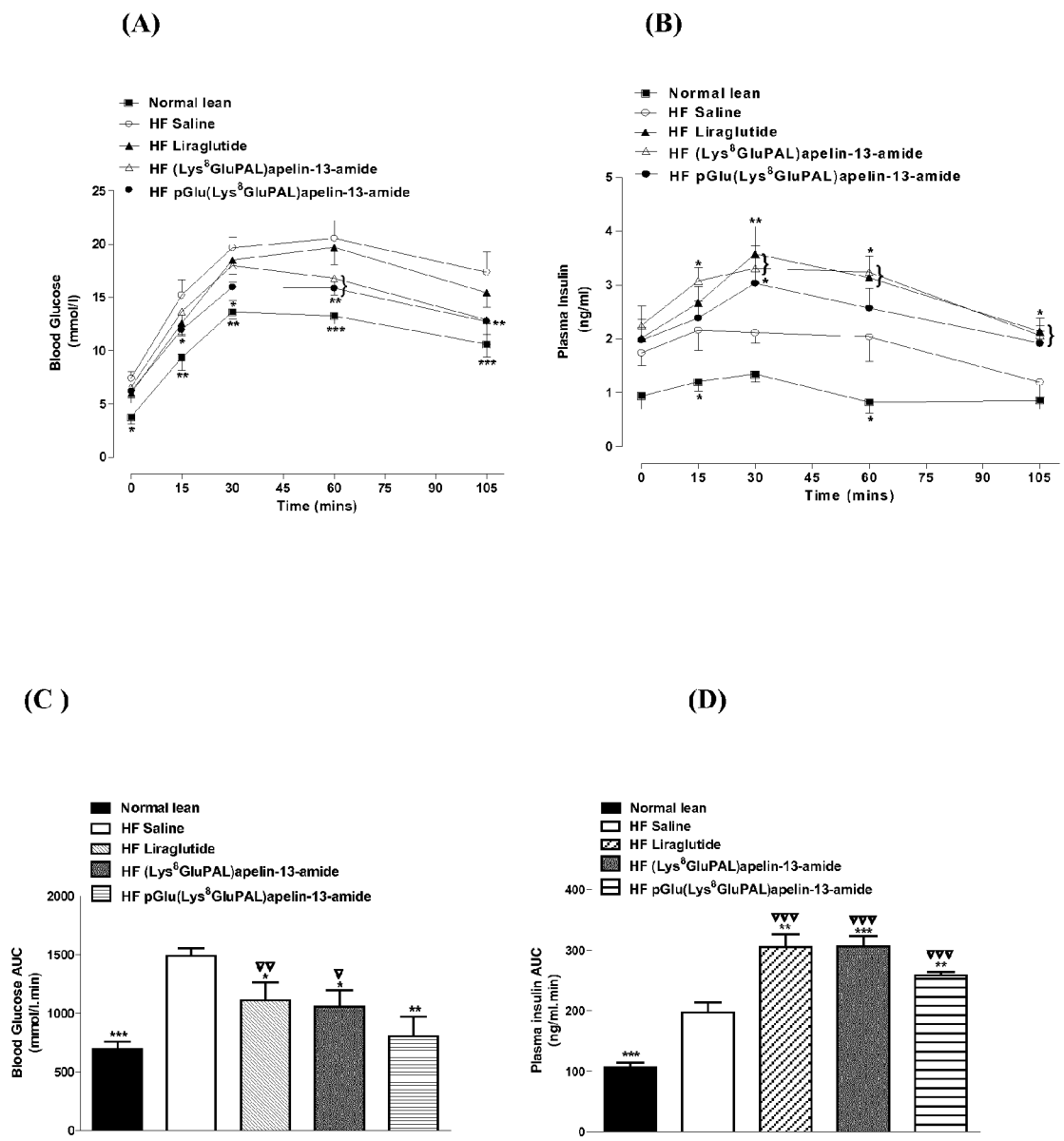
Fig. 27 Chronic 28 day study showing effects of once daily administration of liraglutide, (Lys$^8$gluPAL)apelin-13-amide and pGlu(Lys$^8$gluPAL)apelin-13-amide on (A) blood glucose and (B) plasma insulin in response to an i.p. glucose challenge in high-fat fed NIH Swiss mice.

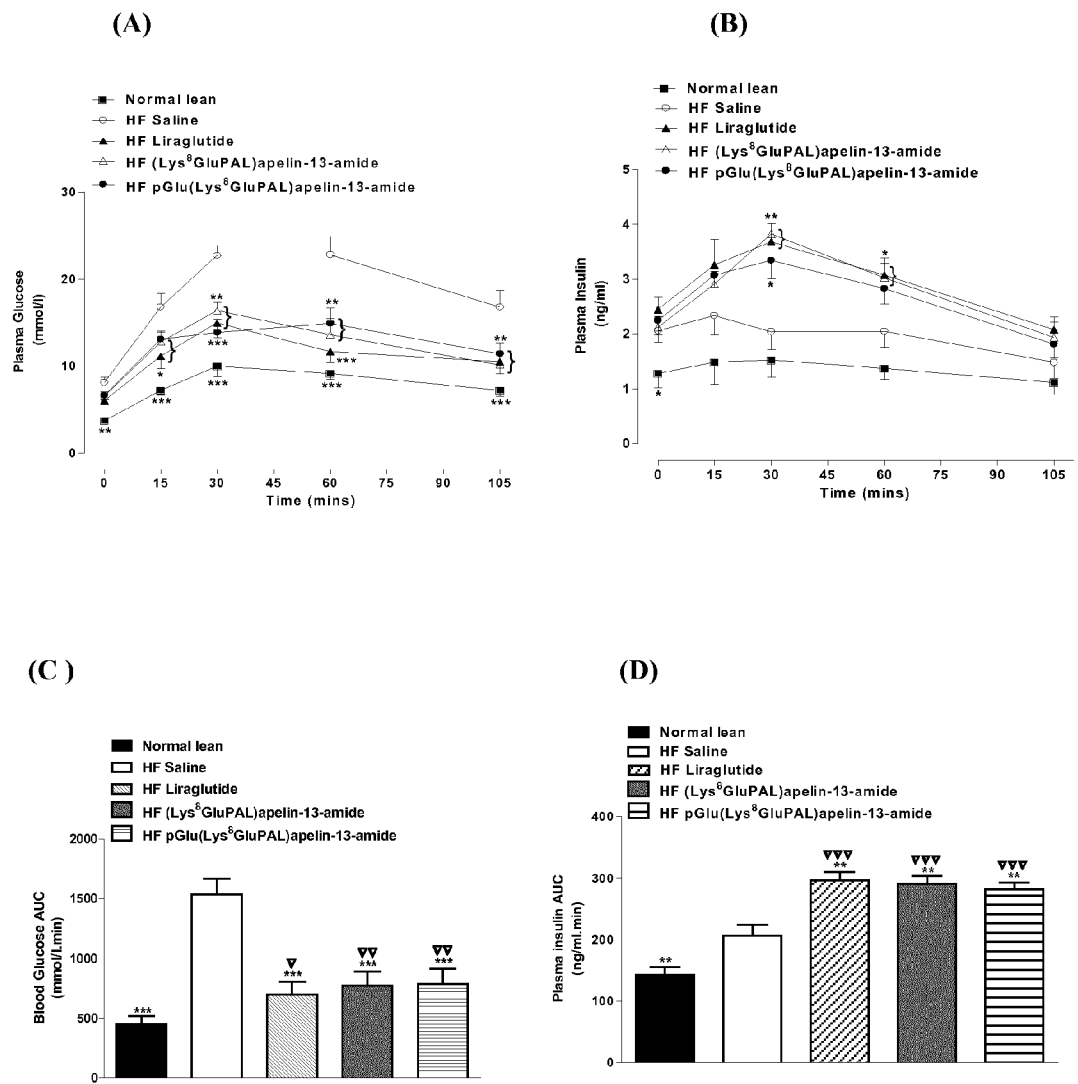
Fig. 28 Chronic 28 day study showing effects of once daily administration of liraglutide, (Lys$^8$gluPAL)apelin-13-amide and pGlu(Lys$^8$gluPAL)apelin-13-amide (A) blood glucose and (B) plasma insulin in response to an oral glucose challenge in high-fat fed NIH Swiss mice.

Fig. 29 Chronic 28 day study showing effects of once daily administration of liraglutide, (Lys$^8$gluPAL)apelin-13-amide and pGlu(Lys$^8$gluPAL)apelin-13-amide on (A) blood glucose and (B) plasma insulin in response to feeding in high-fat fed NIH Swiss mice.
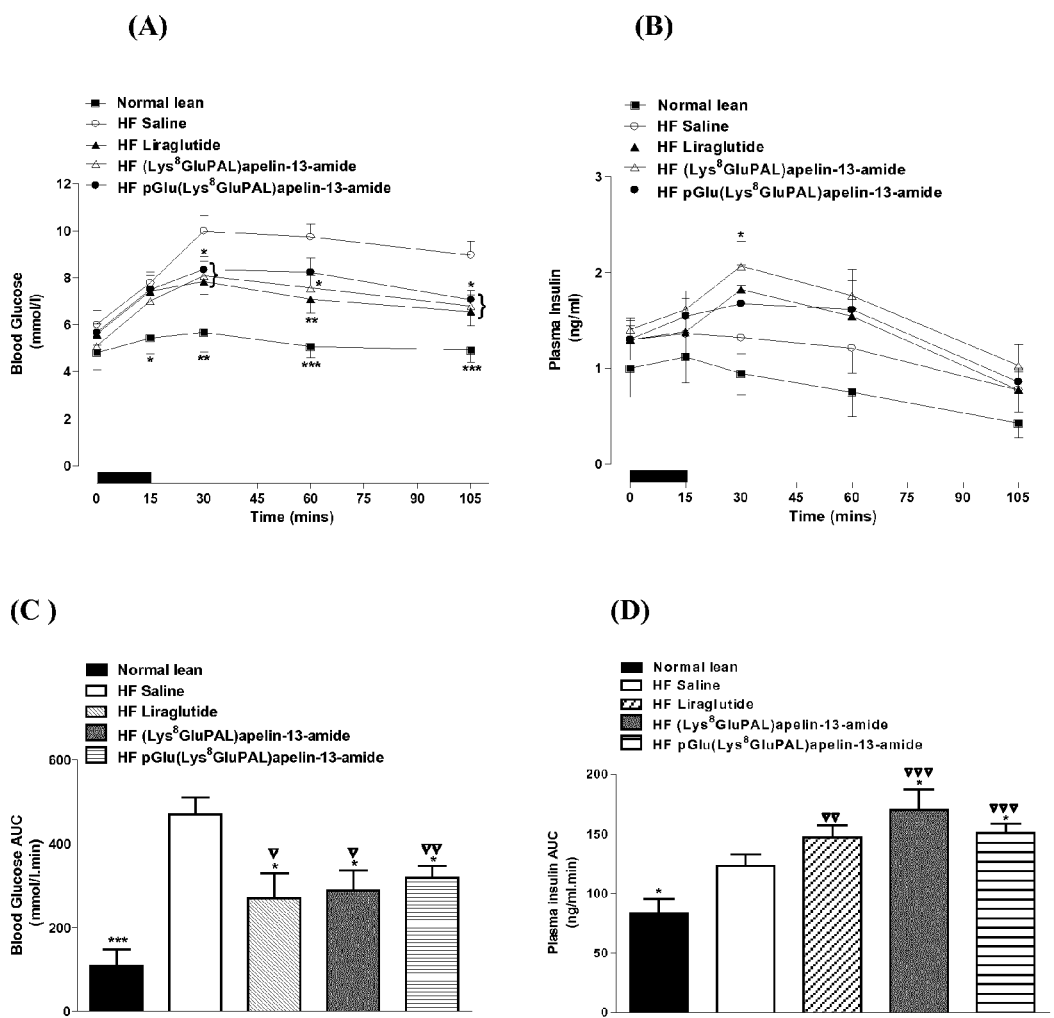

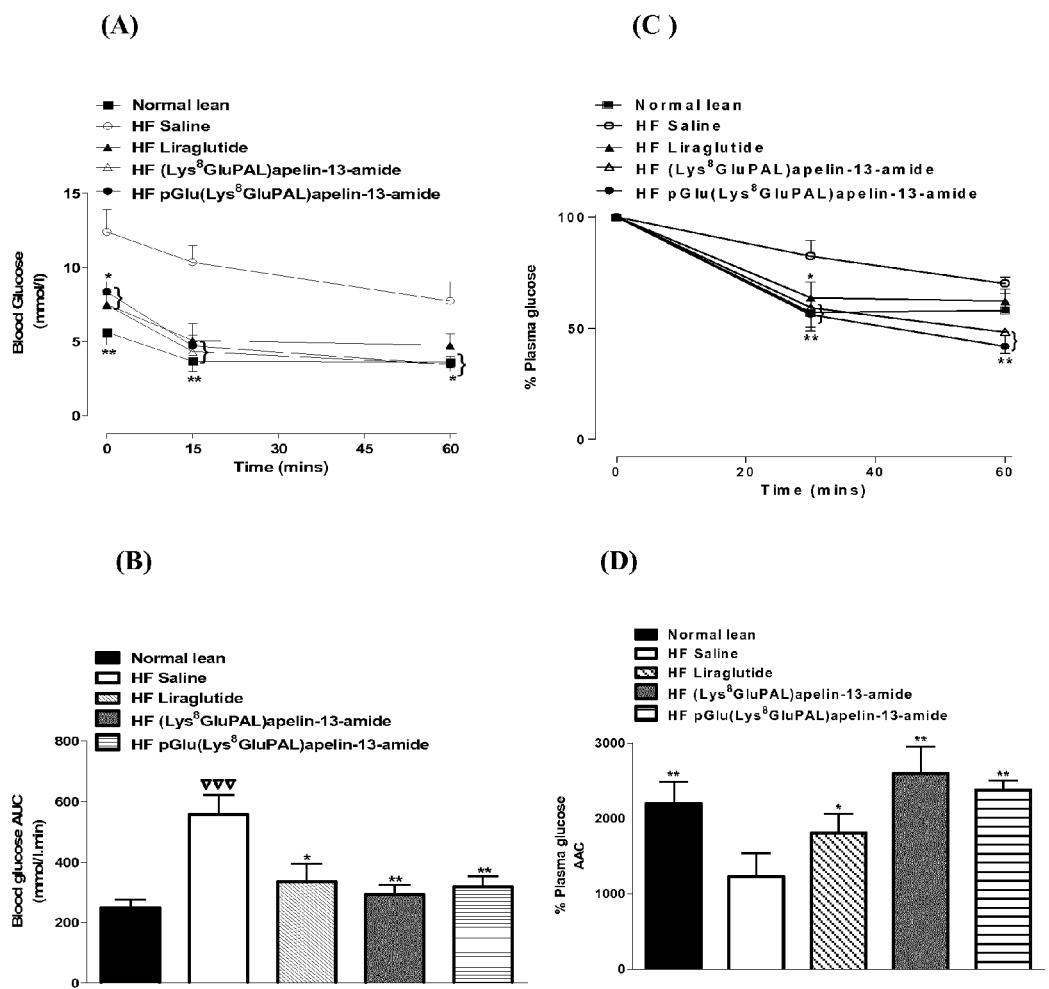
Fig. 30 Chronic 28 day study showing effects of once daily administration of liraglutide, (Lys$^8$gluPAL)apelin-13-amide and pGlu(Lys$^8$gluPAL)apelin-13-amide on blood glucose in response to insulin sensitivity in high-fat fed NIH Swiss mice.

Fig. 31 Chronic 28 day study showing effects of once daily administration of liraglutide, (Lys$^8$gluPAL)apelin-13-amide and pGlu(Lys$^8$gluPAL)apelin-13-amide on glycated haemoglobin (HbA1c) in high-fat fed NIH Swiss mice.

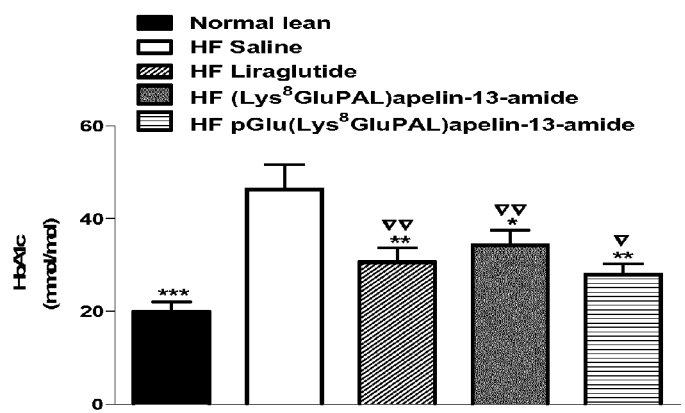

Fig. 32 Chronic 28 day study showing effects of once daily administration of liraglutide, (Lys$^8$gluPAL)apelin-13-amide and pGlu(Lys$^8$gluPAL)apelin-13-amide on (A) bodyweight and (B) percentage fat mass as measured by DEXA scanning in high-fat fed NIH Swiss mice.

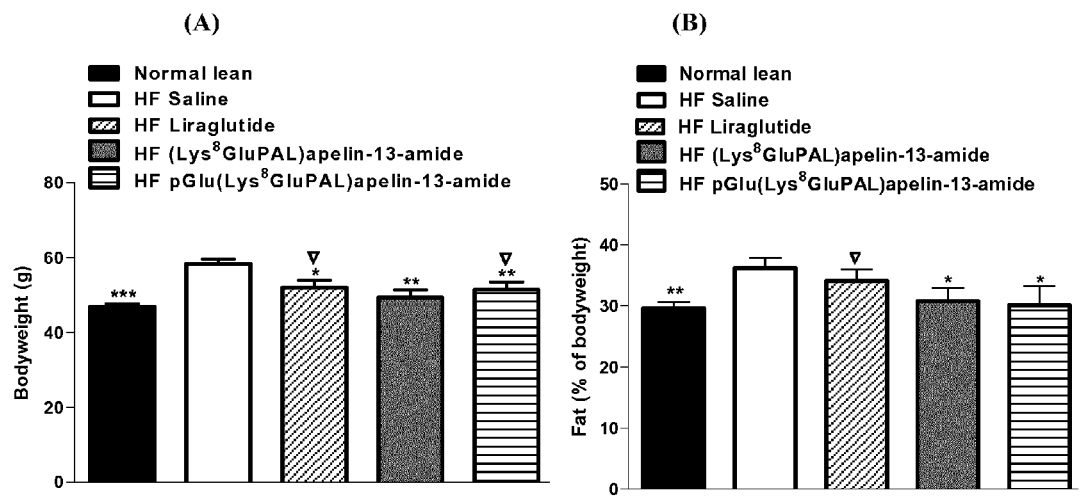

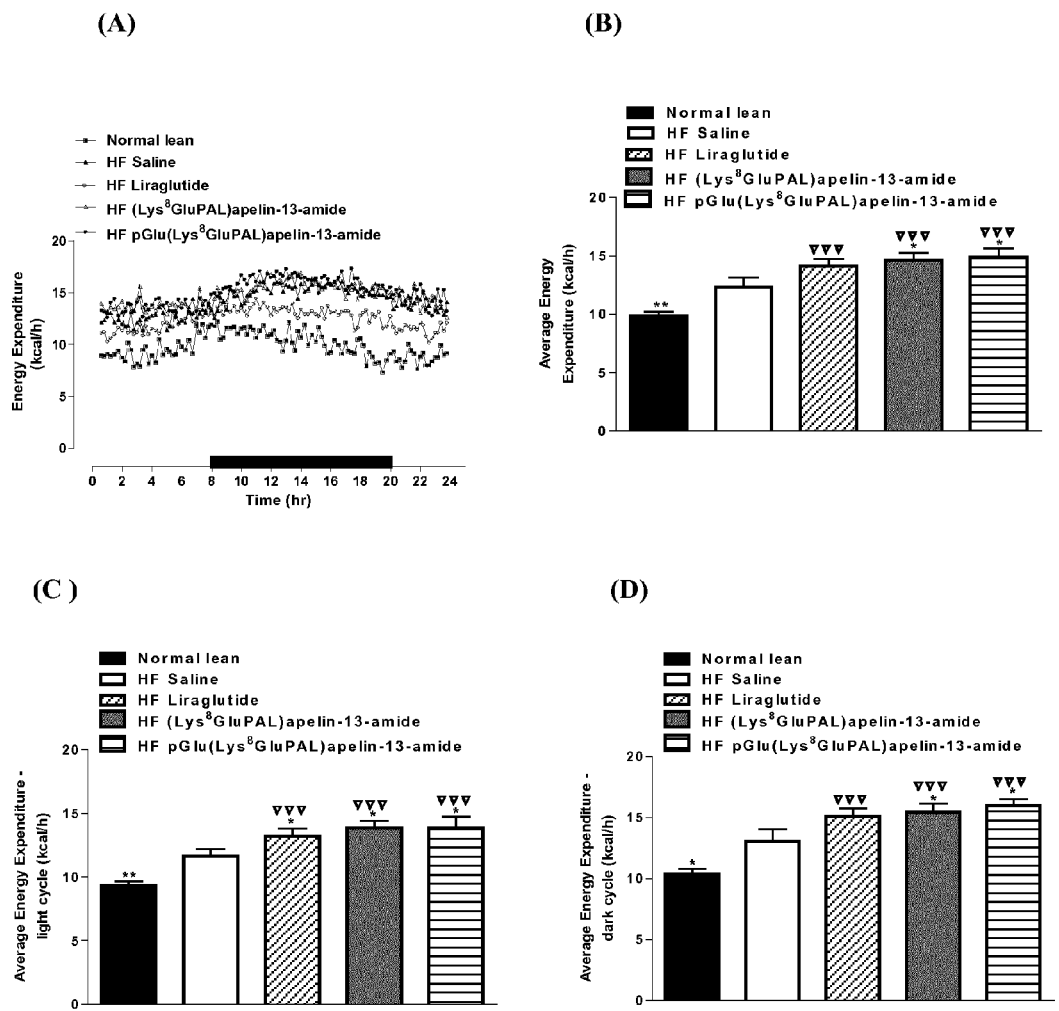
Fig. 33 Chronic 28 day study showing effects of once daily administration of liraglutide, (Lys$^8$gluPAL)apelin-13-amide and pGlu(Lys$^8$gluPAL)apelin-13-amide on energy expenditure in high-fat fed NIH Swiss mice.

Fig. 34 Effects of once daily administration of liraglutide, (Lys$^8$gluPAL)apelin-13-amide and pGlu(Lys$^8$gluPAL)apelin-13-amide on (A) total cholesterol and (B) triglycerides in high-fat fed NIH Swiss mice.
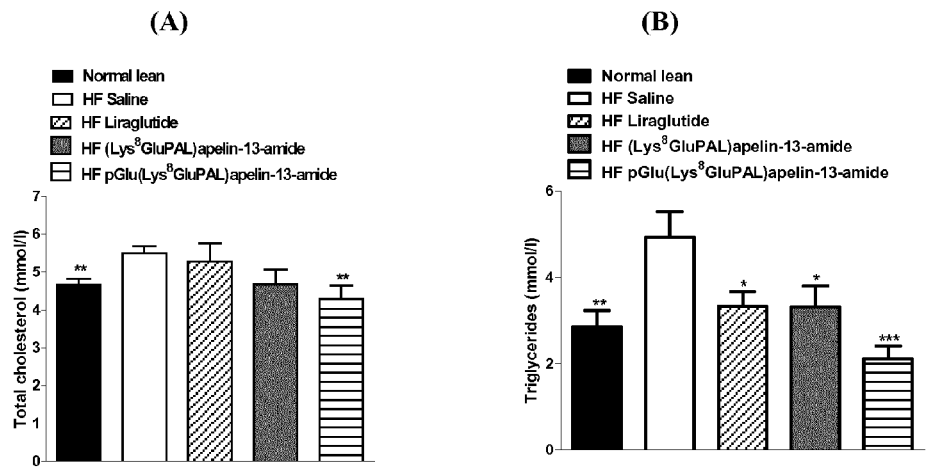
Fig. 35 Effects of once daily administration of liraglutide, (Lys$^8$gluPAL)apelin-13-amide and pGlu(Lys$^8$gluPAL)apelin-13-amide on (A) HDL and (B) LDL in high-fat fed NIH Swiss mice.
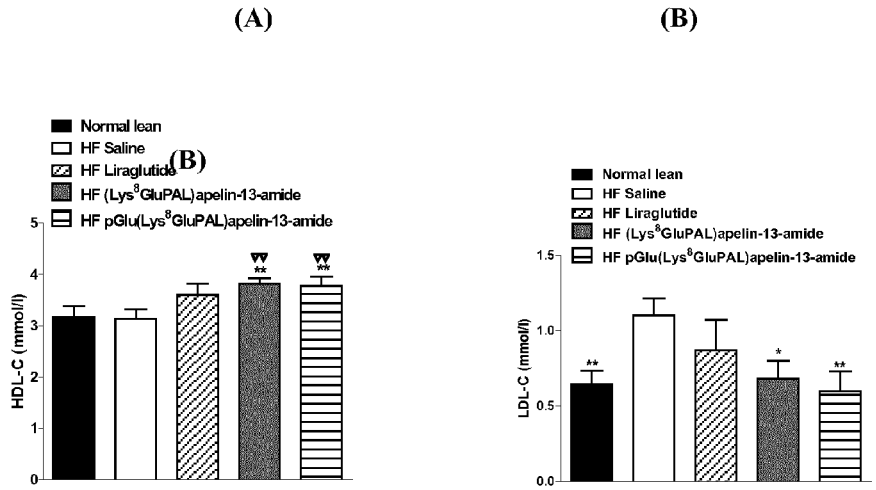

Fig. 36 Effect of apelin-13 and (pGlu)apelin-13 analogues on food intake
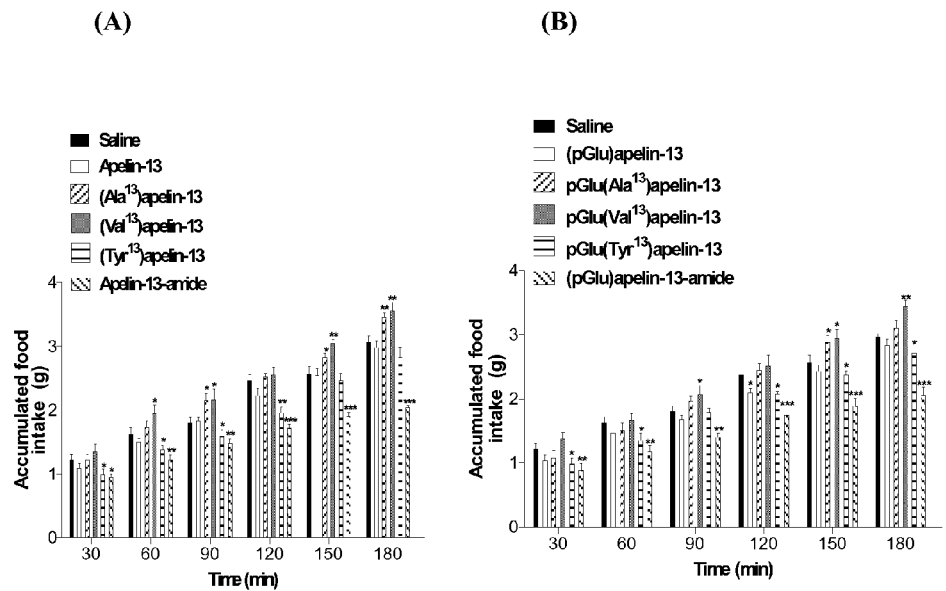
Fig. 37 Dose-dependent effect of apelin-13 and (pGlu)apelin-13 on food intake
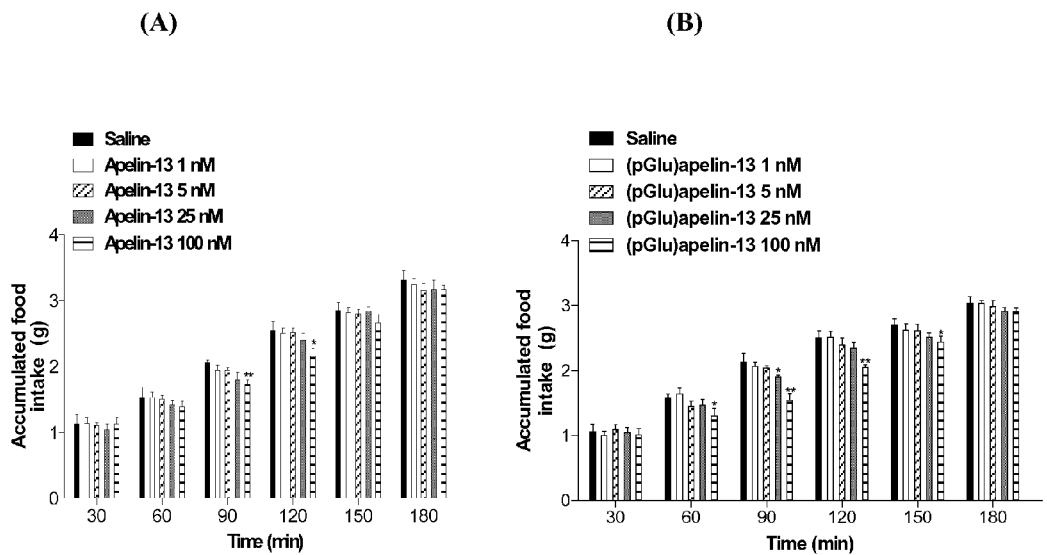

Fig. 38 Dose-dependent effect of apelin-13-amide and (pGlu)apelin-13-amide on food intake
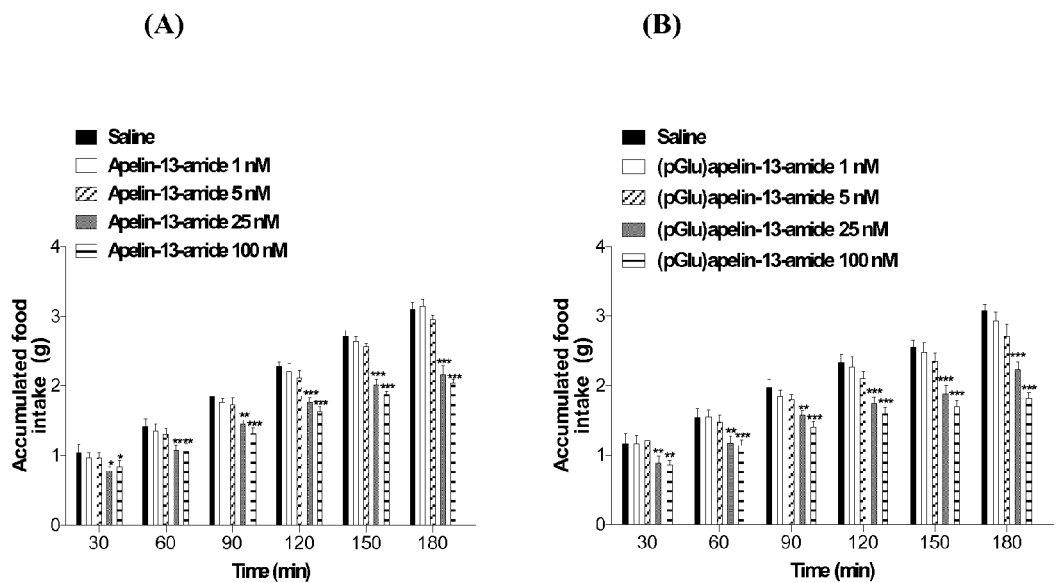
Fig. 39 Effect of fatty acid derived apelin analogues on food intake
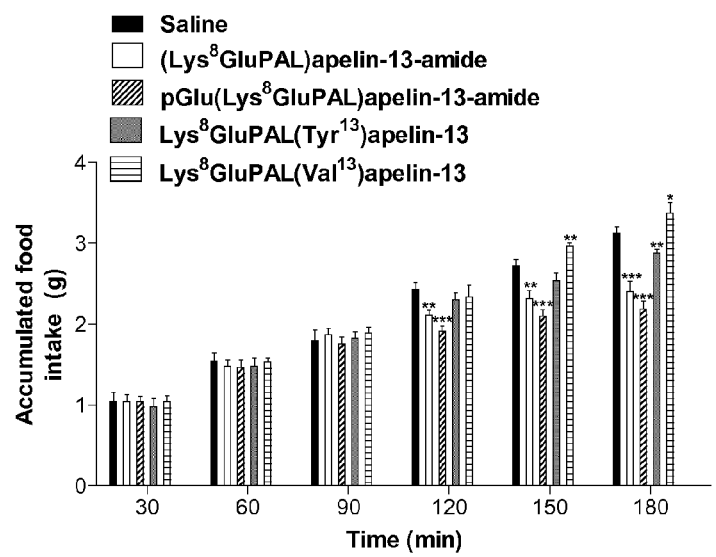

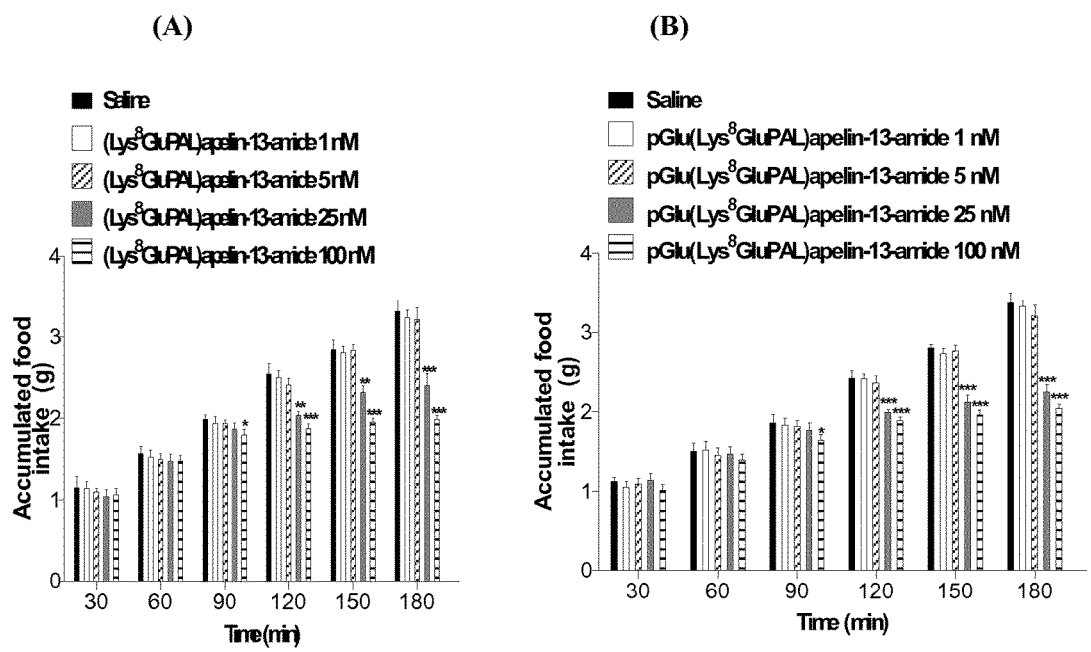
Fig. 40 Dose-dependent effect of fatty acid derived apelin-13 analogues on food intake

APELIN ANALOGUES

CROSS-REFERENCE TO RELATED APPLICATIONS

This application is a Submission Under 35 U.S.C. § 371 for U.S. National Stage Patent Application of, and claims priority to, International Application Number PCT/EP2015/059288 entitled APELIN ANALOGUES, filed Apr. 29, 2015, which is related to and claims priority from Great Britain Patent Application Number 1407532.9, filed Apr. 29, 2014, the entirety of all of which are incorporated herein by reference.

This invention relates to a peptide analogue of apelin, a pharmaceutical composition comprising the same and a method of treatment comprising administering the same.

Apelin is a circulating cytokine produced and secreted by the adipocyte and thus is considered an adipokine (Boucher et al. 2005). Apelin was first discovered from bovine stomach extracts as an endogenous ligand for the orphan receptor APJ (Tatemoto et al. 1998). It is a product of APLN gene and translated as a 77 amino-acid prepropeptide. The prepropeptide is subsequently cleaved to form several bioactive peptides denoted by their length, including apelin-12, -13, -16, -17, -19 and -36. The last 23 residues of the C-terminus of apelin are identical in mammals (Pitkin et al. 2010) implying an important physiological role for these peptides. Studies using synthetic peptides have revealed that apelin-13 and apelin-36 may be the most abundant and biologically active fragments (Kawamata et al. 2001) and structural studies have shown that APJ has 31% structural similarity with angiotensin receptor I. In addition, apelin-36 is degraded to apelin-13 by angiotensin-converting enzyme-related carboxypeptidase 2—ACE2 (Vickers et al. 2002). However, this cleavage is unlikely to inactivate the peptide as several studies have shown that apelin-12 (i.e., apelin-13 minus phenylalanine (Phe) at the C-terminus) has similar binding affinity and activity at the APJ receptor to native apelin-13, suggesting that there are other inactivation pathways beyond that of ACE2. Interestingly, an alanine substitution of the C-terminal Phe of apelin-13 not only blocks the degradative effect of ACE2, but also generates an antagonist at the APJ receptor. Co-injection of $(Ala^{13})$apelin-13 and apelin-13 completely blocks the vasodilator effects of apelin-13 in rats (Lee et al. 2005). No studies as yet have tested the effects of $(Ala^{13})$apelin-13 on insulin secretion and food intake. Both apelin and APJ expression have been localized in the hypothalamus in the anterior pituitary and around the supraoptic and paraventricular nuclei suggesting involvement in hormone release and regulation of food and water intake. Indeed, i.c.v. administration of apelin-13 decreased food intake in fed and starved rats (Sunter et al. 2003). A similar effect was observed with apelin-12 during nocturnal administration, while acute day-time i.c.v. injections increased food intake (O'Shea et al. 2003). A study by Valle and colleagues (2008) showed that i.c.v. injection of apelin-13 for more than 10 days increased food intake, locomotor activity and body temperature in mice. In contrast, intraperitoneal (i.p.) administration of apelin-13 for 10 days showed little effect in food intake, yet dose dependently inhibited body weight gain in rats (Higuchi et al. 2007). Hence, apelin may participate in the regulation of food intake in animals, but further studies are required to determine the exact mechanisms.

In the hypothalamus, apelin has been involved in the regulation of fluid homeostasis by inhibiting the electrical activity of vasopressin-releasing neurons (Lee et al. 2005). However, studies regarding the effect of apelin on water intake have yielded variable results. Central and systemic injections of apelin increased water intake in water-depleted rats (Valle et al. 2008), but an inhibitory effect on drinking has been found in rats deprived for water for 48 h (Pitkin et al. 2010). Mitra and co-workers (2006) found no reliable effect on water intake after central or peripheral administrations of pharmacological doses of (pGlu)apelin-13.

Outside the CNS, apelin mRNA has been detected in a wide range of tissues including vascular endothelial cells, stomach, kidney, lung, mammary gland and adipose tissue in rodents and humans (Sörhede Winzell et al. 2005; Quazi et al. 2009). Similarly, APJ mRNA has been detected in multiple organs including lung, heart, adipose tissue, small intestine, colonic mucosa, ovaries, thyroid gland and hypothalamus (Pitkin et al. 2010) and hence, like many other peptides, apelin has been suggested to possess multiple physiological roles. In the gut, apelin-13 and apelin-36 stimulate gastric cell proliferation. Apelin-12, -13 and -19 induce CCK-release from murine enteroendocrine STC-1 cells (Sörhede Winzell et al. 2005). Apelin immunoreactivity has been detected in oxyntic cells in the rat stomach suggesting that apelin might function as a luminal CCK-releasing factor. Since CCK binds to CCK1R receptors on the local vagus fibres decreasing gastric emptying and increasing satiety, apelin could modulate post-prandial CCK signalling (Pitkin et al. 2010).

Apelin is thought to have numerous biological actions on feeding behaviour, glucose utilization and insulin secretion. Recently, Ringstrom and colleagues (2010) found apelin receptors localised on pancreatic β-cells with some expression in α-cells. There are a number of reports linking apelin to glucose homeostasis but these have conflicting results. This is seen as Ringstrom and co-workers (2010) report that apelin-36 can both stimulate and inhibit insulin secretion depending on the concentration of the peptide. However, Dray and colleagues (2008) report that acute intravenous (i.v.) injection of apelin-13 (2000 pmol/kg every 45 min for 3.75 hours) has a powerful glucose-lowering effect and improved glucose uptake in insulin-sensitive tissues. A food intake study by Valle and colleagues (2008) showed that apelin-13 (1 μg/day) increased food intake significantly on days 3-7. In contradiction, Sunter and co-workers (2003) report no change in food intake after i.v. infusion of $10^{-10}$ M apelin-13 in either fed or fasted Wistar rats. It is also dependent on the location of the injection as to the response of apelin on glucose homeostasis. Therefore, it is assumed that apelin-13 plays a central role in both glucose homeostasis and the control of feeding behaviour but the exact mechanisms of action are currently unknown. Studies have suggested that the most potent isoform of apelin is the N-terminally pyroglutamated form of apelin-13 (pGlu-apelin-13), which is considered the main biological ligand (Zhu et al. 2011). These workers also concluded that apelin is necessary for the maintenance of systemic insulin sensitivity in vivo. Also, apelin production in adipose tissue is strongly upregulated by insulin, and research shows plasma concentrations are increased in obese and hyperinsulinaemic mice and humans (Pitkin et al. 2010).

Many beneficial activities have been ascribed to apelin related peptides, including a protective role in cardiovascular disease (Liu et al. 2013), promoting glucose uptake in cardiac muscle (Xu et al. 2012), is protective in diabetic nephropathy (Pitkin et al. 2010) and it inhibits adipogenesis of pre-adipocytes and lipolysis in mature adipocytes by different mechanisms (Valle et al. 2008). It has been reported that apelin has many vascular benefits (Kidoya & Takakura 2012), reduces the extent of atherosclerotic lesions in ApoE$^{-/-}$ mice, as well as reducing the development of abdominal aortic aneurysms (Chun et al. 2008). Previous research has shown that apelin peptides alter blood pressure, feeding behaviour, pituitary hormone release and can have a neuroprotective effect (Cheng et al. 2012). Apelin has also emerged as a new player with potent functions in energy metabolism, and in improving insulin sensitivity (Castan-Laurell et al. 2008). Overall, apelin appears as a beneficial adipokine with anti-obesity and anti-diabetic properties, which can improve insulin sensitivity and glucose utilization and thus has a promising therapeutic profile in combating these metabolic disorders.

A range of apelin-13 related peptide analogues have been synthesised for antidiabetic testing to assess their antidiabetic potential in both in vitro and in vivo. The activities of a series of apelin analogues were tested by examining their stability in mouse plasma. Longer term chronic effects of twice daily i.p. apelin analogue and select fatty acid derivatives was examined for the most promising selected analogues in high fat fed mice.

SUMMARY OF THE INVENTION

According to a first aspect of the invention, there is provided a peptide analogue comprising at least residues 2-13 of SEQ ID NO: 1 and further comprising a substitution and/or modification at residue 13 of SEQ ID NO: 1.

Optionally, the peptide analogue consists of residues 2-13 of SEQ ID NO: 1.

Optionally, the substitution at residue 13 is selected from the group consisting of Tyr, Thi (β[2-thienyl]-alanine), 4-azido-Phe, 4-cyano-Phe, or Trp; optionally, Tyr.

Optionally, the residue 13 is the C-terminal residue and the modification at residue 13 is the substitution of the terminal carboxyl group by an amide group.

Optionally, the peptide analogue comprises at least residues 1-13 of SEQ ID NO: 1 or consists of residues 1-13 of SEQ ID NO: 1.

Optionally, the peptide analogue further comprises an N-terminal addition of pGlu (5-oxoproline), an acetyl, acyl or acylated moiety; optionally pGlu (5-oxoproline).

Optionally, the peptide analogue further comprises a modification at residue 8 of SEQ ID NO: 1, wherein, further optionally, the modification at residue 8 is the addition of a fatty acid group to residue 8. Further optionally, the fatty acid group is a $C_{12}$ to $C_{20}$ fatty acid, optionally a $C_{16}$ fatty acid (palmitate), linked to residue 8 by a bivalent linker, optionally, a γ-glutamyl linker. Optionally, those amino acids present at positions 2-7 and 9-12 of the peptide analogue are unsubstituted with respect to the corresponding residues of SEQ ID NO:1.

Optionally, the substitution at residue 13 is selected from the group consisting of Val or Ala.

Optionally, the peptide analogue is an agonist and is selected from the group comprising (Tyr$^{13}$)apelin-13, Apelin-13-amide, (pGlu)apelin-13, pGlu (Tyr$^{13}$)apelin-13, (pGlu)apelin-13-amide, Lys$^8$GluPAL(Tyr$^{13}$)apelin-13, (Lys$^8$GluPAL)apelin-13-amide, pGlu(Lys$^8$GluPAL)apelin-13-amide; further optionally, from the group comprising (Lys$^8$GluPAL)apelin-13-amide and pGlu(Lys$^8$GluPAL)apelin-13-amide.

Alternatively, the peptide analogue is an antagonist and is selected from the group comprising (Ala$^{13}$)apelin-13, (Val$^{13}$)apelin-13, pGlu (Ala$^{13}$)apelin-13 and pGlu (Val$^{13}$)apelin-13; optionally, from the group comprising pGlu (Ala$^{13}$)apelin-13 and pGlu (Val$^{13}$)apelin-13.

For the avoidance of doubt, either the substitution at residue 13 is selected from the group consisting of Tyr, Thi (β[2-thienyl]-alanine), 4-azido-Phe, 4-cyano-Phe, or Trp or the substitution at residue 13 is selected from the group consisting of Val or Ala. In addition or alternatively, residue 13 is the C-terminal residue and the modification at residue 13, if present, is the substitution of the terminal carboxyl group by an amide group, provided that the peptide analogue is not (Ala$^{13}$)apelin-13.

According to a second aspect of the invention, there is provided a pharmaceutical composition comprising the peptide analogue of the first aspect of the invention in association with a pharmaceutically acceptable excipient.

According to a third aspect of the invention, there is provided a method of treating diabetes, the method comprising administering to an individual the peptide analogue of the first aspect of the invention. Optionally, the diabetes is type 2 diabetes.

According to a fourth aspect of the invention, there is provided a method of stimulating insulin release, the method comprising administering to an individual the peptide analogue of the first aspect of the invention.

According to a fifth aspect of the invention, there is provided a method of moderating blood glucose excursions, the method comprising administering to an individual the peptide analogue of the first aspect of the invention.

According to a further aspect of the invention, there is provided a method of increasing food intake or increasing body weight, the method comprising administering to an individual the peptide analogue of the first aspect of the invention.

According to a further aspect of the invention, there is provided a peptide analogue of the first aspect of the invention for use in treating diabetes. Optionally, the diabetes is type 2 diabetes.

According to a further aspect of the invention, there is provided a peptide analogue of the first aspect of the invention for use in stimulating insulin release.

According to a further aspect of the invention, there is provided a peptide analogue of the first aspect of the invention for use in moderating blood glucose excursions.

As used herein, pGlu refers to:

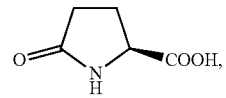

whose carboxylic acid group forms a peptide bond with the amide of the N-terminal residue.

Analogues of apelin-13 may have an enhanced capacity to stimulate insulin secretion, enhance glucose disposal, delay glucose absorption or may exhibit enhanced stability in plasma as compared to native GIP. They also may have enhanced resistance to degradation.

Any of these properties will enhance the potency of the analogue as a therapeutic agent.

The pharmaceutical compositions of the invention are intended for delivery through transdermal, nasal inhalation, oral or injected routes. The peptide analogues of the invention can be administered alone or in combination therapy with native or derived analogues of liraglutide (marketed under the brand name Victoza and developed by Novo Nordisk), exendin-4 (1-39) (Exenatide (INN, marketed as Byetta, Bydureon)) or the like.

Without being bound by theory, a peptide analogue comprising at least residues 2-13 of SEQ ID NO: 1 and further comprising a substitution and/or modification at residue 13 of SEQ ID NO: 1, wherein the substitution at residue 13 is selected from the group consisting Tyr, Thi (β[2-thienyl]-alanine), 4-azido-Phe, 4-cyano-Phe, or Trp; optionally, Tyr acts as an agonist.

Surprisingly, a peptide analogue, with or without N-terminal addition of pGlu, comprising at least residues 2-13 of SEQ ID NO: 1 and further comprising a substitution and/or modification at residue 13 of SEQ ID NO: 1, wherein the substitution at residue 13 is selected from the group consisting Ala or Val acts as an antagonist.

BRIEF DESCRIPTION OF DRAWINGS

The embodiments of the present invention will now be described, by way of example, with reference to the accompanying drawings, in which:

FIG. 1 illustrates stability of various apelin-13 related analogues after incubation with plasma from fasted normal mice. (A) shows percentage of intact peptide after 0, 2, 4, 8 and 24 h (n=2). Values represent mean±SEM. *P<0.05, P<0.01 and *P<0.001 compared to apelin-13 at each time point. (B) shows area under the curve (AUC) analysis for each analogue. Values represent mean±SEM. ***P<0.001 compared to apelin-13.

FIG. 2 illustrates sequences of various apelin-13 analogues. Arrows indicate point on primary sequence where the respective peptides bonds were cleaved following exposure to plasma from fasted normal NIH Swiss mice.

FIG. 3 illustrates stability of various (pGlu)-apelin-13 related analogues after incubation with fasted normal mouse plasma. (A) shows percentage of intact peptide after 0, 2, 4, 8 and 24 h (n=2). Values represent mean±SEM. *P<0.05, P<0.01 and *P<0.001 compared to (pGlu)apelin-13 at each time point. (B) shows area under the curve analysis for each analogue. Values represent mean±SEM. ***P<0.001 compared to (pGlu)apelin-13.

FIG. 4 illustrates sequences of various (pGlu)apelin-13 analogues. Arrows indicate point on the primary sequence where the respective peptides are degraded following exposure plasma from fasted normal NIH Swiss mice.

FIG. 5 illustrates acute effects of (A+B) apelin-13 and (C+D) (pGlu)apelin-13 related analogues on glucose-lowering and insulin release in high fat fed NIH Swiss mice with dietary-induced diabetes. Plasma glucose and plasma insulin concentrations were measured prior to and after i.p. administration of glucose alone (18 mmol/kg body weight), or in combination with apelin analogues (25 nmol/kg body weight) in 18 h fasted mice fed a high-fat diet for 150 days. Values represent mean±SEM for eight mice (n=8). *P<0.05, P<0.01 and *P<0.001 compared to glucose alone.

FIG. 6 illustrates effect of i.p. administration of glucose alone (18 mmol/kg body weight), (Ala$^{13}$)apelin-13 and (Tyr$^{13}$)apelin-13 alone or in combination (each 25 nmol/kg body weight) on (A) blood glucose and (B) plasma insulin in 18 h fasted mice fed a high-fat diet for 150 days. Values represent mean±SEM for eight mice (n=8). *p<0.05 and **p<0.01 compared to glucose alone, $^+$P<0.05 compared to (Tyr$^{13}$)apelin-13, $^\nabla$P<0.05 and $^{\nabla\nabla}$P<0.01 compared to (Ala$^{13}$).

FIG. 7 illustrates effect of i.p. administration of glucose alone (18 mmol/kg body weight), (Val$^{13}$)apelin-13 and (Tyr$^{13}$)apelin-13 alone or in combination (each 25 nmol/kg body weight) on (A) blood glucose and (B) plasma insulin in 18 h fasted mice fed a high-fat diet for 150 days. Values represent mean±SEM for eight mice (n=8). *P<0.05 and **P<0.01 compared to glucose alone, $^+$P<0.05 and $^{++}$P<0.01 compared to (Tyr$^{13}$)apelin-13, $^\nabla$P<0.05 compared to (Val$^{13}$) apelin-13.

FIG. 8 illustrates effect of i.p. administration of glucose alone (18 mmol/kg body weight), (Ala$^{13}$)apelin-13 and Apelin-13-amide alone or in combination (each 25 nmol/kg body weight) on (A) blood glucose and (B) plasma insulin in 18 h fasted mice fed a high-fat diet for 150 days. Values represent mean±SEM for eight mice (n=8). *P<0.05 and **p<0.01 compared to glucose alone, $^+$P<0.05 and $^{++}$P<0.01 compared to Apelin-13-amide, $^\nabla$P<0.05 and $^{\nabla\nabla}$P<0.01 compared to (Ala$^{13}$)apelin-13.

FIG. 9 illustrates effect of i.p. administration of glucose alone (18 mmol/kg body weight), (Val$^{13}$)apelin-13 and Apelin-13-amide alone or in combination (each 25 nmol/kg body weight) on (A) blood glucose and (B) plasma insulin in 18 h fasted mice fed a high-fat diet for 150 days. Values represent mean±SEM for eight mice (n=8). *P<0.05 and **P<0.01 compared to glucose alone, $^+$P<0.05, $^{++}$P<0.05 and $^{+++}$P<0.001 compared to Apelin-13-amide, $^\nabla$P<0.05 compared to (Val$^{13}$)apelin-13.

FIG. 10 illustrates tests conducted 2 h after administration of apelin related analogues (25 nmol/kg body wt) in 18 h fasted mice fed a high-fat diet for 150 days. (A) Blood glucose and (B) plasma insulin was measured before and after i.p. administration of glucose (18 mmol/kg body wt) alone or in combination with apelin analogues. Values represent mean±SEM for eight mice (n=8). *P<0.05 and **P<0.01 compared to glucose alone.

FIG. 11 illustrates tests conducted 8 h after administration of apelin related analogues (25 nmol/kg body wt) in 18 h fasted mice fed a high-fat diet for 150 days. (A) Blood glucose and (B) plasma insulin was measured before and after i.p. administration of glucose (18 mmol/kg body wt) alone or in combination with apelin analogues. Values represent mean±SEM for eight mice (n=8). *P<0.05 and **P<0.01 compared to glucose alone.

FIG. 12 illustrates acute effects of fatty acid modified apelin analogues on glucose-lowering and insulin release in high fat fed Swiss NIH mice with dietary-induced diabetes. (A) Blood glucose and (B) plasma insulin concentrations were measured prior to and after i.p. administration of glucose alone (18 mmol/kg body weight), or in combination with apelin analogues (25 nmol/kg body weight) in 18 h fasted mice fed a high-fat diet for 150 days. Values represent mean±SEM for eight mice (n=8). *P<0.05, compared to glucose alone.

FIG. 13 illustrates tests conducted 16 h after administration of fatty acid apelin analogues (25 nmol/kg body wt) in mice fed a high-fat diet for 150 days. (A) Blood glucose and (B) plasma insulin was measured before and after i.p. administration of glucose (18 mmol/kg body wt) alone or in combination with apelin analogues. Values represent mean±SEM for eight mice (n=8). *P<0.05, P<0.01 and *P<0.001 compared to glucose alone.

FIG. 14 illustrates effects of twice daily administration of saline, exendin-4(1-39), apelin-13-amide and (pGlu)apelin-13-amide (each at 25 nmol/kg bw) on (A) bodyweight and (B) bodyweight change (%) during a 28 day study in high fat fed NIH Swiss mice. The black horizontal bar represents the treatment period. Values represent mean±S.E.M. (n=8) where *P<0.05, and ***P<0.001 is compared to high-fat fed saline treated mice, $^{\nabla\nabla}$P<0.01 and $^{\nabla\nabla\nabla}$P<0.001 is compared to normal control mice.

FIG. 15 illustrates chronic effects of twice daily administration of saline, exendin-4(1-39), apelin-13-amide and (pGlu)apelin-13-amide (each at 25 nmol/kg bw) on (A) cumulative food intake and (B) energy intake during a 28 day study in high fat fed NIH Swiss mice. Values represent mean for cumulative food intake±S.E.M. (n=8) where *P<0.01 and ***P<0.001 is compared to high-fat fed saline treated mice.

FIG. 16 illustrates chronic effects of twice daily administration of saline, exendin-4(1-39), apelin-13-amide and (pGlu)apelin-13-amide (each at 25 nmol/kg bw) on (A) blood glucose (B) and plasma insulin during a 28 day study in high fat fed NIH Swiss mice. The black horizontal bar represents the treatment period. Values represent mean±S.E.M. (n=8) where *P<0.05, P<0.01 and *P<0.001 is compared to high-fat fed saline treated mice.

FIG. 17 illustrates ipGTT tests performed in high fat fed NIH Swiss mice following 28 days of twice daily i.p. administration of saline ((0.9% w/v) NaCl), exendin-4(1-39), apelin-13-amide and (pGlu)apelin-13-amide (each at 25 nmol/kg bw). Mice were fasted for 18 h previously. (A) Blood glucose and (B) plasma insulin concentrations were measured prior to and after i.p. administration of glucose alone (18 mmol/kg bw). Values represent the mean±S.E.M. (n=8) where *P<0.05, P<0.01 and *P<0.001 is compared to high-fat fed saline treated mice, $^{\triangledown\triangledown}$P<0.01 and $^{\triangledown\triangledown\triangledown}$P<0.001 is compared with normal mice.

FIG. 18 illustrates OGGT tests performed in high fat fed NIH Swiss mice following 28 days of twice daily i.p. administration of saline ((0.9% w/v) NaCl), exendin-4(1-39), apelin-13-amide and (pGlu)apelin-13-amide (each at 25 nmol/kg bw). Mice were fasted for 18 h previously. (A) Blood glucose and (B) plasma insulin concentrations were measured prior to and after oral administration of glucose alone (18 mmol/kg bw). Glucose and insulin AUC values (C+D) for 0-60 min are also included. Values represent the mean±S.E.M. (n=8) where *P<0.05, P<0.01 and *P<0.001 is compared to high-fat fed saline treated mice, $^{\triangledown}$P<0.05, $^{\triangledown\triangledown}$P<0.01 and $^{\triangledown\triangledown\triangledown}$P<0.001 is compared to normal mice.

FIG. 19 illustrates response to feeding tests performed in high fat fed NIH Swiss mice following 28 days of twice daily i.p. administration of saline ((0.9% w/v) NaCl), exendin-4(1-39), apelin-13-amide and (pGlu)apelin-13-amide (each at 25 nmol/kg bw). Mice were fasted for 18 h previously and given free access to normal diet for 15 min. (A) Blood glucose and (B) plasma insulin concentrations were measured at t=0, 15, 30, 60 and 105 min and time of feeding is represented by the black horizontal bar. Glucose and insulin AUC data (C+D) for 0-60 min are also shown. Values represent the mean±S.E.M. (n=8) where *P<0.05, P<0.01 and *P<0.001 is compared to high-fat fed saline treated mice, $^{\triangledown}$P<0.05, $^{\triangledown\triangledown}$P<0.01 and $^{\triangledown\triangledown\triangledown}$P<0.001 is compared to normal mice.

FIG. 20 illustrates insulin sensitivity tests performed in high fat fed NIH Swiss mice following 28 days of saline ((0.9% w/v) NaCl), exendin-4(1-39), apelin-13-amide and (pGlu)apelin-13-amide (each at 25 nmol/kg bw). Insulin (25 U/kg bw) was administered by i.p. injection at t=0 min (A+B). The % plasma glucose area above curve (AAC) values for 0-60 min post-injection are also shown (C+D). Values represent the means±S.E.M. (n=8) where *P<0.05 and **P<0.01 is compared to high-fat fed saline treated mice, $^{\triangledown}$P<0.05 is compared to normal mice.

FIG. 21 illustrates result of glycated haemoglobin test performed in high fat fed NIH Swiss mice following 28 days of saline ((0.9% w/v) NaCl), exendin-4(1-39), apelin-13-amide and (pGlu)apelin-13-amide (each at 25 nmol/kg bw). Blood was taken from the tail vein of each mouse and measurements recorded by Bayer A1CNow$^+$ multi-test system. Values represent the means±S.E.M. (n=8) where *P<0.05 and **P<0.01 compared to high-fat fed saline treated mice, $^{\triangledown}$P<0.05 and $^{\triangledown\triangledown}$P<0.01 is compared to normal mice.

FIG. 22 illustrates chronic effects of twice-daily i.p. administration of saline ((0.9% w/v) NaCl), exendin-4(1-39), apelin-13-amide and (pGlu)apelin-13-amide (each at 25 nmol/kg bw) following 28 day administration on (A) bodyweight (at end of study) and (B) fat mass (%) in high-fat fed, control and treated, and lean control mice. Values represent the mean±S.E.M. (n=6) where *P<0.05 and ***P<0.001 is compared to high-fat fed saline treated mice, $^{\triangledown}$P<0.05 and $^{\triangledown\triangledown\triangledown}$P<0.001 is compared to normal mice.

FIG. 23 illustrates chronic effects in high fat fed NIH Swiss mice of twice-daily i.p. administration of saline ((0.9% w/v) NaCl), exendin-4(1-39), apelin-13-amide and (pGlu)apelin-13-amide (each at 25 nmol/kg bw) following 28 day administration on energy expenditure (A+B). Mice were placed in CLAMS metabolic chambers for 24 h (12 h dark period as shown by the black bar) and energy expenditure calculated using RER with the following equation: $(3.815+1.232 \times RER) \times VO2$. Values represent the mean±S.E.M. (n=6) where *P<0.05 is compared to high-fat fed saline treated mice. Separate light and dark cycle AUC values are also shown (C+D).

FIG. 24 illustrates chronic effects in high fat fed NIH Swiss mice of once daily administration of saline, liraglutide, (Lys$^8$gluPAL)apelin-13-amide and pGlu(Lys$^8$gluPAL)apelin-13-amide (each at 25 nmol/kg bw) on (A) bodyweight and (B) bodyweight change (%) during the 28 day study. The black horizontal bar represents the treatment period. Values represent mean±S.E.M. (n=8) where *P<0.05, P<0.01 and *P<0.001 is compared to high-fat saline treated mice, $^{\triangledown\triangledown}$P<0.01 and $^{\triangledown\triangledown\triangledown}$P<0.001 is compared to normal mice.

FIG. 25 illustrates chronic effects in high fat fed NIH Swiss mice of once daily administration of saline, liraglutide, (Lys$^8$gluPAL)apelin-13-amide and pGlu(Lys$^8$gluPAL)apelin-13-amide (each at 25 nmol/kg bw) on (A) cumulative food intake and (B) energy intake during the 28 day study. Values represent mean for cumulative food intake and energy intake±S.E.M. (n=8) where *P<0.05, P<0.01 and *P<0.001 is compared to high-fat saline treated mice.

FIG. 26 illustrates chronic effects in high fat fed NIH Swiss mice of once daily administration of saline, liraglutide, (Lys$^8$gluPAL)apelin-13-amide and pGlu(Lys$^8$gluPAL)apelin-13-amide (each at 25 nmol/kg bw) on (A) blood glucose and (B) plasma insulin during the 28 day study. The black horizontal bar represents the treatment period. Values represent mean±S.E.M. (n=8) where *P<0.05, P<0.01 and *P<0.001 is compared to high-fat saline treated mice.

FIG. 27 illustrates ipGTT tests performed in high fat fed NIH Swiss mice following 28 days of once daily i.p. administration of saline ((0.9% w/v) NaCl), liraglutide, (Lys$^8$gluPAL)apelin-13-amide and pGlu(Lys$^8$gluPAL)apelin-13-amide (each at 25 nmol/kg bw). Mice were fasted for 18 h previously. (A) Blood glucose and (B) plasma insulin concentrations were measured prior to and after i.p. administration of glucose alone (18 mmol/kg bw). Glucose and insulin AUC values (C+D) for 0-60 min are also included. Values represent the mean±S.E.M. (n=8) where *P<0.05, P<0.01 and *P<0.001 is compared to high-fat saline treated mice, $^{\triangledown}$P<0.05, $^{\triangledown\triangledown}$P<0.01 and $^{\triangledown\triangledown\triangledown}$P<0.001 is compared with normal mice.

FIG. 28 illustrates OGTT tests performed in high fat fed NIH Swiss mice following 28 days of once daily i.p. administration of saline ((0.9% w/v) NaCl), liraglutide, (Lys$^8$gluPAL)apelin-13-amide and pGlu(Lys$^8$gluPAL)apelin-13-amide (each at 25 nmol/kg bw). Mice were fasted for 18 h previously. (A) Blood glucose and (B) plasma insulin concentrations were measured prior to and after oral administration of glucose alone (18 mmol/kg bw). Glucose and insulin AUC values (C+D) for 0-60 min are also included. Values represent the mean±S.E.M. (n=8) where *P<0.05, P<0.01 and *P<0.001 is compared to high-fat saline treated mice, $^∇$P<0.05, P<0.01 and $^{∇∇∇}$P<0.001 is compared to normal mice.

FIG. 29 illustrates response to feeding tests performed in high fat fed NIH Swiss mice following 28 days of once daily i.p. administration of saline ((0.9% w/v) NaCl), liraglutide, (Lys$^8$gluPAL)apelin-13-amide and pGlu(Lys$^8$gluPAL)apelin-13-amide (each at 25 nmol/kg bw). Mice were fasted for 18 h previously and given free access to normal diet for 15 min. (A) Blood glucose and (B) plasma insulin concentrations were measured at t=0, 15, 30, 60 and 105 min and time of feeding is represented by the black horizontal bar. Glucose and insulin AUC values (C+D) for 0-60 min are also shown. Values represent the mean±S.E.M. (n=8) where *P<0.05, P<0.01 and *P<0.001 is compared to high-fat saline treated mice, $^∇$P<0.05, $^{∇∇}$P<0.01 and $^{∇∇∇}$P<0.001 is compared to normal mice.

FIG. 30 illustrates insulin sensitivity tests performed in high fat fed NIH Swiss mice following 28 days of saline ((0.9% w/v) NaCl), liraglutide, (Lys$^8$gluPAL)apelin-13-amide and pGlu(Lys$^8$gluPAL)apelin-13-amide (each at 25 nmol/kg bw) (A+B). Insulin (25 U/kg bw) was administered by intraperitoneal injection at t=0 min. The % plasma glucose AAC values for 0-60 min post-injection are also shown (C+D). Values represent the means±S.E.M. (n=8) where *p<0.05, P<0.01 and *P<0.001 is compared to high-fat saline treated mice, $^{∇∇∇}$P<0.001 is compared to normal mice.

FIG. 31 illustrates result of glycated haemoglobin test performed in high fat fed NIH Swiss mice following 28 days of saline ((0.9% w/v) NaCl), liraglutide, (Lys$^8$gluPAL)apelin-13-amide and pGlu(Lys$^8$gluPAL)apelin-13-amide (each at 25 nmol/kg bw). Blood was taken from the tail vein of each mouse and measurements recorded by Bayer A1CNow$^+$ multi-test system. Values represent the means±S.E.M. (n=8) where *P<0.05, p<0.01 and *p<0.001 is compared to high-fat saline treated mice, $^∇$P<0.05 and $^{∇∇}$P<0.01 is compared to normal mice.

FIG. 32 illustrates chronic effects in high fat fed NIH Swiss mice of once daily i.p. administration of saline ((0.9% w/v) NaCl), liraglutide, (Lys$^8$gluPAL)apelin-13-amide and pGlu(Lys$^8$gluPAL)apelin-13-amide (each at 25 nmol/kg bw) following 28 day administration on (A) bodyweight (at end of study) and (B) fat mass (%) in high-fat fed saline control, peptide treated, and lean control mice. Values represent the mean±S.E.M. (n=6) where *P<0.05, P<0.01 and *P<0.001 is compared to high-fat saline treated mice, $^∇$P<0.05 is compared to normal mice.

FIG. 33 illustrates chronic effects in high fat fed NIH Swiss mice of once daily i.p. administration of saline ((0.9% w/v) NaCl), liraglutide, (Lys$^8$gluPAL)apelin-13-amide and pGlu(Lys$^8$gluPAL)apelin-13-amide (each at 25 nmol/kg bw) following 28 day administration on energy expenditure (A+B). Mice were placed in CLAMS metabolic chambers for 24 hours (12 hour dark period as shown by the black bar) and average energy expenditure as well as dark and light phase energy expenditure calculated using RER with the following equation: $(3.815+1.232×RER)×VO_2$. Values represent the mean±S.E.M. (n=6) where *P<0.05 and **P<0.01 is compared to high-fat saline treated mice, $^{∇∇∇}$P<0.001 is compared to normal mice. Separate light and dark cycle AUC values are also shown (C+D).

FIG. 34 illustrates the effects of once daily administration of liraglutide, (Lys$^8$gluPAL)apelin-13-amide and pGlu(Lys$^8$gluPAL)apelin-13-amide on (A) total cholesterol and (B) triglycerides in high-fat fed NIH Swiss mice. Values represent the mean±S.E.M. (n=8) where *P<0.05, P<0.01 and *P<0.001 is compared with high-fat fed mice.

FIG. 35 illustrate the Effects of once daily administration of liraglutide, (Lys$^8$gluPAL)apelin-13-amide and pGlu(Lys$^8$gluPAL)apelin-13-amide on (A) HDL-C and (B) LDL-C in high-fat fed NIH Swiss mice. Values represent the mean±S.E.M. (n=8) where *P<0.05 and **P<0.01 is compared with high-fat fed controls, $^{∇∇}$p<0.01 is compared with lean controls.

FIG. 36 illustrates (A) effect of apelin-13 analogues (25 nmol/kg) and (B) effect of (pGlu)apelin-13 analogues (25 nmol/kg) on voluntary food intake in male NIH Swiss mice. Saline and peptide analogues were administered by intraperitoneal injection and cumulative food intake was monitored at 30, 60, 90 and 120 min after feeding. Values are mean±SEM (n=8). *P<0.05, P<0.01 and P<0.001 compared to saline control group.

FIG. 37 illustrates (A) acute dose-response effects of apelin-13 (1-100 nmol/kg) and (B) acute dose-response effects of (pGlu)apelin-13 (1-100 nmol/kg) on voluntary food intake in male NIH Swiss mice. Saline and peptide analogues were administered by intraperitoneal injection and cumulative food intake was monitored at 30, 60, 90 and 120 min after feeding. Values are mean±SEM (n=8). *P<0.05 and **P<0.01 compared to saline control group.

FIG. 38 illustrates (A) acute dose-response effects of apelin-13-amide (1-100 nmol/kg) and (B) acute dose-response effects of (pGlu)apelin-13-amide (1-100 nmol/kg) on voluntary food intake in male NIH Swiss mice. Saline and peptide analogues were administered by intraperitoneal injection and cumulative food intake was monitored at 30, 60, 90 and 120 min after feeding. Values are mean±SEM (n=8). *P<0.05 and **P<0.01 compared to saline control group.

FIG. 39 illustrates the effect of (Lys$^8$GluPAL)apelin-13-amide, pGlu(Lys$^8$GluPAL)apelin-13-amide, Lys$^8$GluPAL(Tyr$^{13}$)apelin-13 and Lys$^8$GluPAL(Val$^{13}$)apelin-13 (25 nmol/kg) on voluntary food intake in male NIH Swiss mice. Saline and peptide analogues were administered by intraperitoneal injection and cumulative food intake was monitored at 30, 60, 90 and 120 min after feeding. Values are mean±SEM (n=8). *P<0.05 and **P<0.01 compared to saline control group.

FIG. 40 illustrates (A) acute dose-response effects of various fatty acid derived apelin-13 analogues (1-100 nmol/kg) and (B) acute dose-response effects of various fatty acid derived (pGlu)apelin-13 analogues (1-100 nmol/kg) on voluntary food intake in male NIH Swiss mice. Saline and peptide analogues were administered by intraperitoneal injection and cumulative food intake was monitored at 30, 60, 90 and 120 min after feeding. Values are mean±SEM (n=8). *P<0.05 and **P<0.01 compared to saline control group.

MATERIALS AND METHODS

Degradation of Apelin Peptides by Plasma from Fasted Normal NIH Swiss Mice

Apelin peptides (>95% purity; 100 µg) were incubated in vitro at 37° C. on an orbital shaker in 50 mM triethanolamine buffer (370 µl; pH 7.4), with 10 µl of fasted normal mouse plasma (collected from 18 h fasted NIH Swiss mice) for 0, 2, 4, 8 and 24 h. The enzymatic reaction was stopped by adding 50 µl of 10% TFA (0.1% v/v; Sigma-Aldrich Ltd, (Poole, Dorset, UK) and frozen at −20° C. until separation. The terminated reaction products were then applied to an analytical Vydac C-8 column (4.6×150 mm; Phenomenex, Macclesfield, Cheshire, UK) for rp-HPLC analysis. The absorbance was monitored at 214 nm using a Spectrasystem UV 2000 detector (Thermoquest Limited, Manchester, UK) and the traces were recorded by Thermo Electron ChromQuest data collection software (version 4). HPLC peak fractions were collected manually and subjected to MALDI-TOF mass spectrometry for peptide identification.

Characterisation of Apelin Peptides Using Matrix Assisted Laser Desorption Ionisation Time of Flight Mass Spectrometry (MALDI-TOF MS).

All purchased peptides were checked and characterised through MALDI-TOF mass spectrometry. An aliquot (1.5 µl) of 1 mg/ml of peptide sample was applied to one well of a 100-well stainless steel sample plate. A further 1.5 µl of matrix solution (10 mg/ml solution of was mixed with the peptide sample and allowed to dry at room temperature. The mass spectra were recorded using a Voyager-DE BioSpectrometry Workstation (PerSeptive Biosystems, Framingham, Mass., USA). Masses were recorded as a mass-to-charge (m/z) ratio against relative peak intensity, and compared with theoretical values.

Acute and Long-Term Effects of Apelin Analogues In Vivo.

NIH Swiss mice (Harlan UK Ltd., Blackthorne, UK) were derived from a nucleus colony obtained from the National Institute of Health, Bethesda, Md., USA. One group of mice were maintained on a standard rodent diet (10% fat, 30% protein, 60% carbohydrate; percent of total energy 12.99 kJ/g, Trouw Nutrition, Cheshire, UK) and used as a model of normal glycaemia. Other NIH Swiss mice were maintained on a high fat diet (45% fat, 20% protein, 35% carbohydrate; percent of total energy 26.15 kJ/g; Dietex, Essex, UK) from 8 weeks of age for 150 days to produce a model of diet induced obesity-diabetes. High-fat fed mice exhibited increased body weight and elevated non-fasting blood glucose compared with mice receiving standard rodent diet (n=8). All mice were housed in an air-conditioned room maintained at 22±2° C. with a 12 h light: 12 h dark cycle (08:00-20:00 h), were singly caged, and selected for experimental groups according to body weight and non-fasted blood glucose. Drinking water and diet were freely available. All animal studies were performed in accordance with the UK Animals (Scientific Procedures) Act 1986.

For acute in vivo studies, blood samples were collected from the cut tip of the tail vain of fasted, conscious mice into fluoride/heparin coated glucose microcentrifuge tubes (Sarstedt, Germany) immediately prior to (t=0) and at 15, 30, 60 and 105 min following i.p. injection of glucose (18 mol/kg bw).

For 28 day long-term study of selected apelin analogues administered twice daily, normal control NIH Swiss and high-fat fed NIH Swiss were grouped and received twice daily i.p. injections of saline vehicle (0.9% NaCl (w/v)) at 09:00 and 17:00 h over a 4 day run-in period. Following the run-in period, normal control (n=8) and high-fat fed mice (n=8) received twice daily (09:00 and 17:00 h) i.p. administration of saline vehicle (0.9% NaCl (w/v)) for 28 days. Additional groups of high-fat fed mice (n=8) received twice daily i.p. injections of apelin-13-amide, (pGlu)apelin-13-amide or exendin-4(1-39) (each at 25 nmol/kg bw) over a 28 day treatment period.

For another 28 day long-term study of selected fatty acid apelin analogues administered once daily, normal control NIH Swiss (n=8) and high-fat fed NIH Swiss (n=8) were grouped and received once daily i.p. injections of saline vehicle (0.9% NaCl (w/v)) at 17:00 h over a 4 day run-in period. Following the run-in period, normal control (n=8) and high-fat fed mice (n=8) received once daily (17:00 h) i.p. administration of saline vehicle (0.9% NaCl (w/v)) for 28 days. Additional groups of high-fat fed mice (n=8) received once daily i.p. injections of (Lys$^8$gluPal)apelin-13-amide, pGlu(Lys$^8$gluPal)apelin-13-amide or liraglutide (each at 25 nmol/kg bw) over a 28 day treatment period.

Measurement of Metabolic Effects from 28 Day Long Term Studies

Food intake, body weight, blood glucose and plasma insulin were monitored at intervals of 2-3 days throughout the run-in and 28 day treatment period. Blood samples for glucose and plasma insulin measurement were collected at intervals throughout the study from the cut tail vein of conscious mice. Following the 28 day treatment period, oral, i.p. and meal test glucose tolerance (18 nmol/kg bw.), and insulin sensitivity (25 U/kg bw) tests were performed. Glucose was measured using an Ascensia Contour meter and blood was collected and processed for plasma insulin analysis by radioimmunoassay. Body weight and fat mass was also assessed using the PIXImus DEXA scanner whilst energy expenditure, intake, food intake and feeding bouts were assessed using the CLAMS metabolic chamber. HbA$_{1c}$ was analysed post 28 days using Bayer A1C Now$^+$ Multi Test meter. Lipid profile test was obtained by using the iLab analyser. Cholesterol, triglyceride and HDL-cholesterol levels were measured, in plasma (3 µl), using the iLab analyser. LDL-cholesterol levels were obtained using the Friedewald equation=total cholesterol−HDL−(triglycerides/3).

Acute Effects of Apelin Analogues of Food Intake

Mice were habituated to a daily feeding regime of 3 h/day by progressively reducing the daily feeding period over 3 weeks. This was performed to ensure mice consumed entire daily food intake within 3 h, thereby allowing "peptide" effects to be measured over the known eating period of mice. On days 1 to 7, mice were supplied with food from 10:00 h to 20:00 h, on days 8 to 14, food was presented from 10:00 h to 19:00 h and on days 15 to 21, food was restricted to the 3 h interval from 10:00 h to 13:00 h. This regime was continued throughout the experimental period.

Mice that were habituated to a 3 h daily feeding regime were administered with an i.p. injection of saline (0.9% w/v NaCl) or apelin peptide (1-100 nmol/kg bw) at 10:00 h (n=8). Immediately following injection, food was initially weighed and then presented to the mice and subsequently weighed at 30 min intervals up to 180 min.

Statistical Analysis

Results are expressed as mean±S.E.M. Data were compared using the Student t-test on Prism GraphPad version 5.0. Area under the curve (AUC) analyses was calculated using the trapezoidal rule with baseline subtraction. P<0.05 was considered to be statistically significant.

TABLE 1

Degradation profile of apelin-13 related analogues.

| Peptide analogue | Peak 1 | Peak 2 |
|---|---|---|
| Apelin-13 | Apelin-13 (1-11) | Apelin-13 (1-12) |
| | $M_r$ = 1307.5 Da | $M_r$ = 1403.6 Da |
| | (1306.5 Da) | (1403.6 Da) |
| | RT = 17.1 min | RT = 18.4 min |
| (Ala$^{13}$)apelin-13 | (Ala$^{13}$)apelin-13 (1-8) | (Ala$^{13}$)apelin-13 (1-11) |
| | $M_r$ = 1020.7 Da | $M_r$ = 1306.5 Da |
| | (1021.1 Da) | (1306.5 Da) |
| | RT = 12.9 min | RT = 14.5 min |
| (Val$^{13}$)apelin-13 | (Val$^{13}$)apelin-13 (1-12) | |
| | $M_r$ = 1403.6 Da | |
| | (1403.6 Da) | |
| | RT = 19.1 min | |
| (Tyr$^{13}$)apelin-13 | (Tyr$^{13}$)apelin-13 (1-7) | (Tyr$^{13}$)apelin-13 (1-12) |
| | $M_r$ = 900.5 Da | $M_r$ = 1404.5 Da |
| | (898.1 Da) | (1403.6 Da) |
| | RT = 13.9 min | RT = 19.5 min |
| Apelin-13-amide | Apelin-13-amide (1-12) | |
| | $M_r$ = 1404.1 Da | |
| | (1403.7 Da) | |
| | RT = 19.5 min | |

Degradation profile of various apelin-13 related analogues: plasma incubations (4 h) were separated on a Vydac C-8 analytical HPLC column and all peaks were collected prior to analysis by MALDI-TOF mass spectrometry. Degradation fragments, actual molecular weights ($M_r$) and retention times (RT) are shown. Theoretical molecular weights of each fragment are shown in brackets.

TABLE 2

Degradation profile of (pGlu)apelin-13 related analogues.

| Peptide analogue | Peak 1 | Peak 2 | Peak 3 |
|---|---|---|---|
| (pGlu)apelin-13 | (pGlu)apelin-13 (1-5) | (pGlu)apelin-13 (1-6) | (pGlu)apelin-13 (1-12) |
| | $M_r$ = 651.7 Da | $M_r$ = 738.6 Da | $M_r$ = 1385.8 Da |
| | (650.8 Da) | (737.8 Da) | (1385.6 Da) |
| | RT = 13.9 min | RT = 17.4 min | RT = 19.3 min |
| pGlu (Ala$^{13}$)apelin-13 | pGlu(Ala$^{13}$)apelin-13 (1-7) | | |
| | $M_r$ = 875.4 Da | | |
| | (875.0 Da) | | |
| | RT = 14.9 min | | |
| pGlu (Val$^{13}$)apelin-13 | pGlu(Val$^{13}$)apelin-13 (1-6) | pGlu(Val$^{13}$)apelin-13 (1-12) | |
| | $M_r$ = 738.9 Da | $M_r$ = 1385.9 Da | |
| | (737.9 Da) | (1385.7 Da) | |
| | RT = 18.0 min | RT = 19.2 min | |
| pGlu (Tyr$^{13}$)apelin-13 | pGlu(Tyr$^{13}$)apelin-13 (1-5) | pGlu(Tyr$^{13}$)apelin-13 (1-6) | pGlu(Tyr$^{13}$)apelin-13 (1-12) |
| | $M_r$ = 651.7 Da | $M_r$ = 739.1 Da | $M_r$ = 1386.0 Da |
| | (650.8 Da) | (737.9 Da) | (1385.7 Da) |
| | RT = 14.2 min | RT = 17.1 min | RT = 19.1 min |
| (pGlu)apelin-13-amide | (pGlu)apelin-13-amide (1-5) | (pGlu)apelin-13-amide (1-12) | |
| | $M_r$ = 652.7 Da | $M_r$ = 1387.6 Da | |
| | (650.8 Da) | (1385.7 Da) | |
| | RT = 17.5 min | RT = 19.2 min | |

Degradation profile of various (pGlu)apelin-13 related analogues: plasma (4 h) incubations were separated on a Vydac C-8 analytical HPLC column and all peaks were collected prior to analysis by MALDI-TOF mass spectrometry. Degradation fragments, theoretical molecular weights ($M_r$) and retention times (RT) are shown. Theoretical molecular weights of each fragment are shown in brackets.

TABLE 3

Percentage of intact peptide remaining after 4 h and estimated half-life ($t_{1/2}$) of apelin peptides.

| Peptide | % intact peptide (4 h) | Half-life ($t_{1/2}$) (h) | Rank order of stability | Significance of $t_{1/2}$ compared to apelin-13 |
|---|---|---|---|---|
| Apelin-36 | 5.5 ± 0.6 | 1.3 | 15 | |
| Apelin-13 | 25.4 ± 1.5 | 2.1 | 14 | |
| Apelin-12 | 39.5 ± 1.9 | 3.4 | 13 | |
| (pGlu)apelin-13 | 47.0 ± 3.2 | 3.8 | 12 | |
| (Val$^{13}$)apelin-13 | 66.5 ± 1.1 | 7.7 | 11 | *** |
| (Tyr$^{13}$)apelin-13 | 76.7 ± 1.3 | 8.5 | 10 | *** |
| pGlu(Val$^{13}$)apelin-13 | 76.2 ± 1.9 | 9.8 | 9 | *** |
| (Ala$^{13}$)apelin-13 | 70.5 ± 2.2 | 10.3 | 8 | *** |
| (pGlu)apelin-13-amide | 85.0 ± 1.3 | 10.4 | 7 | *** |
| pGlu(Ala$^{13}$)apelin-13 | 74.4 ± 5.2 | 11.1 | 6 | *** |
| Apelin-13-amide | 80.4 ± 1.9 | 11.4 | 5 | *** |
| pGlu(Tyr$^{13}$)apelin-13 | 79.0 ± 0.6 | 12.2 | 4 | *** |
| Lys$^8$GluPAL(Tyr$^{13}$)apelin-13 | 100 | >24 | =1 | *** |
| (Lys$^8$GluPAL)apelin-13-amide | 100 | >24 | =1 | *** |
| pGlu(Lys$^8$GluPAL)apelin-13-amide | 100 | >24 | =1 | *** |

Summary Table showing percentage of intact peptide and half-life of apelin related peptide analogues tested. Half-lives were calculated by constructing a graph of percentage intact peptide against time. Linear regression "best-fit" analysis was used to calculate the time at which half of the peptide was degraded. Values are mean ± SEM for 2 independent experiments.
*** P < 0.001 compared to apelin-13.

TABLE 4

Data shows rank order of apelin-13 related analogues in relation to acute glucose lowering and insulinotropic activities in vivo in NIH Swiss mice fed a high-fat diet for 150 days.

| Peptide analogue | Glucose lowering, where glucose alone = 100% | Insulin secretion, where glucose alone = 100% | Rank order on basis of anti-hyperglycaemic efficacy |
|---|---|---|---|
| (Val$^{13}$)apelin-13 ^ | 124% (**) | 68% (*) | 10 |
| (Ala$^{13}$)apelin-13 ^ | 118% (*) | 74% (**) | 9 |
| pGlu(Val$^{13}$)apelin-13 ^ | 116% (*) | 75% (**) | 8 |
| pGlu(Ala$^{13}$)apelin-13 ^ | 110% | 86% (*) | 7 |
| Apelin-13 | 92% | 111% | 6 |
| (pGlu)apelin-13 | 89% | 95% | 5 |
| (Tyr$^{13}$)apelin-13 | 77% (*) | 131% (*) | 4 |
| pGlu(Tyr$^{13}$)apelin-13 | 71% (*) | 138% (**) | 3 |
| Apelin-13-amide | 65% () | 153% (*) | 2 |
| (pGlu)apelin-13-amide | 57% () | 159% (*) | 1 |

Note:
^ denotes peptide antagonists.
(*) $P < 0.05$,
(**) $P < 0.01$ and
(***) $P < 0.001$ compared to blood glucose alone group and plasma insulin glucose alone group respectively.

TABLE 5

Data shows acute effects of (Tyr$^{13}$)apelin-13 and apelin-13-amide, and the antagonistic properties of (Ala$^{13}$)apelin-13 and (Val$^{13}$)apelin-13, alone and in combination, on blood glucose and plasma insulin secretion in NIH Swiss mice fed a high-fat diet for 150 days.

| Peptide | Glucose lowering, where glucose alone = 100% | Insulin secretion, where glucose alone = 100% |
|---|---|---|
| (Tyr$^{13}$)apelin-13 | 77% (*) | 131% (*) |
| Apelin-13-amide | 65% () | 153% (*) |
| (Ala$^{13}$)apelin-13 | 118% (*) | 74% (*) |
| (Val$^{13}$)apelin-13 | 124% () | 68% () |
| (Tyr$^{13}$)apelin-13 + (Ala$^{13}$)apelin-13 | 107% | 96% |
| (Tyr$^{13}$)apelin-13 + (Val$^{13}$)apelin-13 | 109% | 91% |
| Apelin-13-amide + (Ala$^{13}$)apelin-13 | 91% | 107% |
| Apelin-13-amide + (Val$^{13}$)apelin-13 | 107% | 86% (*) |

(*) $P < 0.05$,
(**) $P < 0.01$ and
(***) $P < 0.001$ compared to blood glucose alone group and plasma insulin glucose alone group respectively.

TABLE 6

Data shows rank order of various apelin related analogues on glucose-lowering and plasma insulin secretion in NIH Swiss mice fed a high-fat diet for 150 days following a 2 h delay.

| Peptide agonist | Glucose lowering, where glucose alone = 100% | Insulin secretion, where glucose alone = 100% | Rank order on basis of anti-hyperglycaemic efficacy |
|---|---|---|---|
| (Tyr$^{13}$)apelin-13 | 85% | 116% | 4 |
| pGlu(Tyr$^{13}$)apelin-13 | 78% () | 142% () | 3 |
| Apelin-13-amide | 73% () | 142% () | 2 |
| (pGlu)apelin-13-amide | 67% () | 146% (*) | 1 |

(**) $P < 0.01$ and
(***) $P < 0.001$ compared to blood glucose alone group and plasma insulin glucose alone group respectively.

TABLE 7

Data shows rank order of various apelin related analogues on glucose-lowering and plasma insulin secretion in NIH Swiss mice fed a high-fat diet for 150 days following a 8 h delay.

| Peptide agonist | Glucose lowering, where glucose alone = 100% | Insulin secretion, where glucose alone = 100% | Rank order on basis of anti-hyperglycaemic efficacy |
|---|---|---|---|
| (Tyr$^{13}$)apelin-13 | 91% | 104% | 4 |
| Apelin-13-amide | 88% | 106% | 3 |
| pGlu(Tyr$^{13}$)apelin-13 | 86% (*) | 112% | 2 |
| (pGlu)apelin-13-amide | 79% (*) | 120% (*) | 1 |

(*) $P < 0.05$ compared to blood glucose alone group and plasma insulin glucose alone group respectively.

TABLE 8

Data shows rank order of fatty acid derived apelin agonists in response to insulin secretion and glucose lowering effects in NIH high-fat fed mice fed a high-fat diet for 150 days following acute i.p. glucose tolerance test.

| Peptide agonist | Glucose lowering, where glucose alone = 100% | Insulin secretion, where glucose alone = 100% | Rank order on basis of anti-hyperglycaemic efficacy |
|---|---|---|---|
| pGlu(Lys$^8$GluPAL)apelin-13-amide | 79% | 119% (*) | 1 |
| (Lys$^8$GluPAL)apelin-13-amide | 85% | 110% | 2 |
| Lys$^8$GluPAL(Tyr$^{13}$)apelin-13 | 93% | 104% | 3 |

(*) $P < 0.05$ compared to plasma insulin glucose alone group.

TABLE 9

Data shows rank order of fatty acid derived apelin agonists in response to insulin secretion and glucose lowering effects in NIH high-fat fed mice fed a high-fat diet for 150 days following 16 h delayed i.p. glucose tolerance test.

| Peptide agonist | Glucose lowering, where glucose alone = 100% | Insulin secretion, where glucose alone = 100% | Rank order on basis of anti-hyperglycaemic efficacy |
|---|---|---|---|
| pGlu(Lys$^8$GluPAL)apelin-13-amide | 57% () | 150% (*) | 1 |
| (Lys$^8$GluPAL)apelin-13-amide | 61% () | 156% (*) | 2 |
| Lys$^8$GluPAL(Tyr$^{13}$)apelin-13 | 91% | 126% (*) | 3 |

(*) $P < 0.05$,
(**) $P < 0.01$ and
(***) $P < 0.001$ compared to blood glucose alone group and plasma insulin glucose alone group respectively.

FIG. 36 illustrates (A) apelin-13-amide (25 nmol/kg) reduced food intake from 21.5% to 33.7% over 3 h ($P<0.05$-$P<0.001$) compared to saline treated control. (Val$^{13}$)apelin-13 (25 nmol/kg) acted as an antagonist and increased food intake from 10.7% to 16.0% over 3 h ($P<0.05$ and $P<0.01$) compared to saline treated control. (B) (pGlu)apelin-13-amide (25 nmol/kg) reduced food intake from 27.0% to 32.4% over 3 h ($P<0.01$ and $P<0.001$) compared to saline treated control.
pGlu(Val$^{13}$)apelin-13 (25 nmol/kg) acted as an antagonist and increased food intake from 13.6% to 15.8% over 3 h ($P<0.05$ and $P<0.01$) compared to saline treated control.

FIG. 37 illustrates (A) Apelin-13 (100 nmol/kg) reduced food intake by 16.7% at 90 min ($P<0.01$), however, this effect was not sustainable over 3 h. (B) (pGlu)apelin-13 (100 nmol/kg) reduced food intake from 3.8% to 28.1% at 90 min ($P<0.05$ and $P<0.01$). However, this effect was not sustainable over 3 h.

FIG. 38 illustrates (A) Apelin-13-amide (25 nmol/kg) reduced food intake from 23.2% to 31.3% over 3 h ($P<0.05$-$P<0.001$) compared to saline treated control. Apelin-13-amide (100 nmol/kg) decreased food intake from 19.4% to 34.5% over 3 h ($P<0.05$ and $P<0.01$) compared to saline treated control. (B) (pGlu)apelin-13-amide (25 nmol/kg) reduced food intake from 24.1% to 30.8% over 3 h ($P<0.05$-$P<0.001$) compared to saline treated control. (pGlu)apelin-13-amide (100 nmol/kg) decreased food intake from 26.7% to 41.1% over 3 h ($P<0.01$ and $P<0.001$) compared to saline treated control.

FIG. 39 illustrates (Lys⁸GluPAL)apelin-13-amide (25 nmol/kg) reduced food intake from 12.0% to 23.0% (120 to 180 min; P<0.01 and P<0.001) compared to saline treated control. pGlu(Lys⁸GluPAL)apelin-13-amide (25 nmol/kg) reduced food intake from 20.8% to 30.1% (120 to 180 min; P<0.001) compared to saline treated control. Lys⁸GluPAL (Val¹³)apelin-13 (25 nmol/kg) increased food intake by 9.2% maximally (150 min; P<0.05 and P<0.01) compared to saline treated control.

FIG. 40 illustrates (A) (Lys⁸GluPAL)apelin-13-amide (25 nmol/kg) reduced food intake from 14.5% to 25.7% (120 to 180 min; P<0.01 and P<0.001) compared to saline treated control. (Lys⁸GluPAL)apelin-13-amide (100 nmol/kg) reduced food intake from 9.0% to 40.2% (90 to 180 min; P<0.05-P<0.001) compared to saline treated control. (B) pGlu(Lys⁸GluPAL)apelin-13-amide (25 nmol/kg) reduced food intake from 19.8% to 32.1% (120 to 180 min; P<0.001) compared to saline treated control. pGlu(Lys⁸GluPAL)apelin-13-amide (100 nmol/kg) reduced food intake from 9.6% to 40.3% (90 to 180 min; P<0.05 and P<0.001) compared to saline treated control.

Some of the peptides were tested, in FIGS. 36-40, at various doses. The dose of 25 nmol/kg, which was used for other physiological studies, worked out as effective on reducing food intake. Very often the 25 nmol/kg dose was just as effective as 100 nmol/kg dose.

The analogues are better reducing food intake more than native peptide found in FIG. 37. The fatty acid peptides are a little slower to work but do have notable effects at the later time points. The inventors did not look beyond 3 h because this was the protocol but these fatty acid modified analogues might have longer lasting effects beyond 3 h.

DISCUSSION

Research indicates that the only degradative pathway for apelin analogues is via the Angiotensin Converting Enzyme (ACE) homologue ACE2 (Vickers et al. 2002), which cleaves the C-terminal amino acid on the apelin sequence (Phe¹³). FIG. 2 shows the likely sites of cleavage of apelin-13 analogues and FIG. 4 shows the predicted cleavage of (pGlu)apelin-13 analogues based upon current MALDI-MS fragmentation patterns. This is shown in Tables 1 and 2. Virtually all of the analogues tested show cleavage points at more than one peptide bond within their respective sequences. This is in agreement with Pitkin and colleagues 2010 who reported that (pGlu)apelin-13, lacking the C-terminal phenylalanine, has similar affinity and agonist activity at the APJ receptor in human tissues in vitro suggesting that cleavage of apelin by ACE2 is not the only inactivating step in man. Indeed, El Messari and co-workers (2004) concluded that ACE2 cleavage is unlikely to inactivate apelin peptides because an in vitro structure activity study showed that apelin lacking the C-terminal phenylalanine showed comparable binding and functional activity at the rat apelin receptor expressed in CHO cells.

There has been no published data on the stability of apelin analogues in vitro. The present data highlights the improvement in stability and effectiveness of C-terminus substitutions of Phe to Ala, Tyr, Val and the addition of an amidated C-terminus (FIGS. 1 and 3). The apelin-13 analogues (Val¹³) apelin-13 ($t_{1/2}$ 7.7 h), (Tyr¹³)apelin-13 ($t_{1/2}$ 8.5 h) and apelin-13-amide ($t_{1/2}$ 11.4 h) all show significantly greater intact peptide when incubated with lean mouse plasma compared to native apelin-13 ($t_{1/2}$ 2.1 h) at 2, 4 and 8 h. Indeed, Table 3 indicates that all analogues tested, apart from native (pGlu)apelin-13, apelin-36 and apelin-12 have a significantly longer half-life ($t_{1/2}$) than apelin-13 in rank order with pGlu(Tyr¹³)apelin-13 and apelin-13 amide showing greatest stability (excluding the modified fatty acid analogues at this stage).

To assess the antagonistic properties of (Ala¹³)apelin-13 and (Val¹³)apelin-13, these peptides were administered in vivo, alone and in combination, with two apelin-13 related agonists, (Tyr¹³)apelin-13 and apelin-13-amide (FIG. 6-10; Table 5). Both (Ala¹³)apelin-13 and (Val¹³)apelin-13 blocked the glucose lowering properties of (Tyr¹³)apelin-13 and apelin-13-amide when administered in combination with (Val¹³)apelin-13 appearing to be the most potent antagonist.

Following acute in vivo studies in high-fat fed NIH Swiss mice, it was shown that (pGlu)apelin-13-amide and apelin-13-amide were the most promising APJ receptor agonists at lowering blood glucose and improving glucose tolerance (FIG. 5). These acute in vivo findings are also summarised in Table 4. These 2 analogues also retain efficacy at least 4 h after an i.p. injection in high-fat fed NIH Swiss mice (FIG. 11) with (pGlu)apelin-13-amide retaining efficacy up to 8 h (FIG. 12).

In order to generate a longer acting peptide, fatty acid analogues of apelin-13-amide, (Tyr¹³)apelin-13 and (pGlu) apelin-13-amide were synthesised. A $C_{16}$ palmitate (PAL) group linked to the ε-amino group of lysine (Lys) at position 8 was used. Numerous acylated compounds of GIP and GLP-1 have already been generated, all of which display complete enzymatic stability and an extended pharmacokinetic profile. Incorporation of a fatty acid moiety into a peptide chain facilitates binding to serum proteins, e.g. albumin, and thus prolonging the duration of action. The three fatty acid analogues, Lys⁸GluPAL(Tyr¹³)apelin-13, (Lys⁸GluPAL)apelin-13-amide and pGlu(Lys⁸GluPAL)apelin-13-amide, which all contain a $C_{16}$ fatty acid (PAL) conjugated to Lys⁸ via a glutamic acid linker (Glu), were shown to have significantly greater intact peptide when incubated with lean mouse plasma compared to native apelin-13 ($t_{1/2}$>24 h) (Table 3). Following acute in vivo studies in high-fat fed NIH Swiss mice, it was shown that pGlu(Lys⁸GluPAL)apelin-13-amide and (Lys⁸GluPAL)apelin-13-amide were the most promising when assessed on their ability to lower blood glucose and improve glucose tolerance (FIG. 12) and such activity was retained and even surpassed up to 16 h (FIG. 13). These acute in vivo findings are also summarised in Tables 6-9.

Following the acute in vivo studies, high fat fed male NIH Swiss mice with diet-induced insulin resistance and obesity were used to assess the chronic glucose-lowering and insulinotropic effects of the four most promising analogues in two separate studies, namely apelin-13-amide, (pGlu)apelin-13-amide with their actions compared with a potent GLP-1 agonist, exendin-4(1-39) (FIG. 14-23) and (Lys⁸GluPAL) apelin-13-amide and pGlu(Lys⁸GluPAL)apelin-13-amide with their actions compared with the fatty acid GLP-1 agonist, liraglutide (FIG. 24-35).

Consistent with earlier findings from acute testing, high-fat fed mice displayed a progressive increase in body weight, food intake, and hyperinsulinaemia, coupled with impaired glucose tolerance, as well as decreased insulin secretion and insulin sensitivity (Gault et al. 2007). Twice daily administration of apelin-13-amide and (pGlu)apelin-13-amide significantly decreased bodyweight at approximately day 20 of the study and only (pGlu)apelin-13-amide significantly reduced food intake. (pGlu)apelin-13-amide began to significantly reduce circulating blood glucose and increase plasma insulin concentrations at day 10 of the study, as did exendin-4(1-39) (FIG. 14-16). Both significantly reduced blood glucose concentrations by the end of the study.

(pGlu)apelin-13-amide and exendin-4(1-39) displayed a significant increase to non-fasting plasma insulin levels, whereas apelin-13-amide did not (FIG. 16). (pGlu)apelin-13-amide, apelin-13-amide and exendin-4(1-39) all significantly improved glucose tolerance and plasma insulin excursion following an i.p. and oral glucose load after the 28 day treatment period (FIGS. 17 and 18). In addition, the effect of exendin-4 on blood glucose concentrations following a glucose load is consistent with previous findings utilizing this peptide. Acute findings with (pGlu)apelin-13-amide displayed effective antihyperglycaemic and insulinotropic properties; this was also noted after chronic 28 day administration with the analogue, therefore consolidating effects observed in acute studies. In response to feeding (FIG. 19), (pGlu)apelin-13-amide, exendin-4(1-39) and apelin-13-amide all showed a similar level of reduction of blood glucose concentration and increase in insulin secretion, with (pGlu)apelin-13-amide displaying no significance compared to a normal mouse in relation to blood glucose.

(pGlu)apelin-13-amide significantly improved insulin sensitivity (FIG. 20) and this finding is consistent with Yue and colleagues (2010) who concluded that apelin is necessary for the maintenance of insulin sensitivity in vivo. Indeed, (pGlu)apelin-13-amide also showed a reduction in glycated haemoglobin ($HbA_{1c}$) in comparison to the high-fat fed saline treated controls (FIG. 21).

(pGlu)apelin-13-amide significantly reduced percentage fat mass compared to high-fat fed controls (35.8%) whereas exendin-4 and apelin-13-amide failed to reach significance (FIG. 22B). In addition, (pGlu)apeln-13-amide (11.5 kcal/hr; $P<0.05$) increased energy expenditure compared to HF treated saline group (10.3 kcal/h) (FIG. 23).

Once daily administration of pGlu($Lys^8$GluPAL)apelin-13-amide induced a significant decrease in bodyweight at day 16 of the 28 day study whereas ($Lys^8$GluPAL)apelin-13-amide and liraglutide showed significance at day 21 (FIG. 24A). Indeed, pGlu($Lys^8$GluPAL)apelin-13-amide reduced bodyweight by approximately 7% whereas ($Lys^8$GluPAL)apelin-13-amide and liraglutide reduced bodyweight by approximately 4% and 3% respectively (FIG. 24B). pGlu($Lys^8$GluPAL)apelin-13-amide, ($Lys^8$GluPAL)apelin-13-amide and liraglutide all significantly reduced food intake at day 8 of the study (FIG. 25). ($Lys^8$GluPAL)apelin-13-amide and liraglutide began to significantly reduce circulating blood glucose and increase plasma insulin concentrations at day 10 of the study, whereas pGlu($Lys^8$GluPAL)apelin-13-amide showed significance at day 13 (FIG. 26).

In response to an i.p and oral glucose challenge, liraglutide ($Lys^8$GluPAL)apelin-13-amide and pGlu($Lys^8$GluPAL)apelin-13-amide all significantly improved glucose tolerance and plasma insulin excursion after the 28 day treatment period (FIGS. 27 and 28) with pGlu($Lys^8$GluPAL)apelin-13-amide showing no significant difference in reduction of blood glucose after an i.p glucose challenge when compared to a normal mouse. A similar pattern was observed after a feeding test post treatment period (FIG. 29).

($Lys^8$GluPAL)apelin-13-amide and pGlu($Lys^8$GluPAL) apelin-13-amide significantly improved insulin sensitivity and this effect was greater than seen with liraglutide (FIG. 30). Also, pGlu($Lys^8$GluPAL)apelin-13-amide significantly reduced $HbA_{1c}$ levels towards then lean controls, more than ($Lys^8$GluPAL)apelin-13-amide and liraglutide after only 28 days treatment.

DEXA analysis revealed that ($Lys^8$GluPAL)apelin-13-amide and pGlu($Lys^8$GluPAL)apelin-13-amide significantly reduced percentage fat mass (30.8%; $P<0.05$ and 30.1%; $P<0.05$, respectively) compared to the high fat-fed saline control mice (36.2%) and no significance was observed compared to the lean controls. However, the liraglutide treated mice showed significantly more percentage fat mass compared to the lean controls (FIG. 32).

($Lys^8$GluPAL)apelin-13-amide (15.4 kcal/hr; $p<0.05$) and pGlu($Lys^8$GluPAL)apelin-13-amide (16.0 kcal/hr; $p<0.05$) expended significantly more energy over a 24 h period in the CLAMS chamber than the high fat-fed saline control mice (13.0 kcal/hr) and liraglutide failed to reach significance (FIG. 33). This could explain the significant bodyweight reduction observed with these peptides.

These observations indicate that chronic treatment with (pGlu)apelin-13-amide for 28 days showed enhanced therapeutic properties even compared to treatment with the established incretin therapy exendin-4, which is a well-established GLP-1 mimetic used widely in T2D therapy. Furthermore, chronic treatment with the fatty acid analogue, pGlu($Lys^8$GluPAL)apelin-13-amide for 28 days showed similar and even enhanced therapeutic properties when compared to treatment with the longer acting GLP-1 agonist, liraglutide.

Liraglutide, ($Lys^8$GluPAL)apelin-13-amide and pGlu($Lys^8$GluPAL)apelin-13-amide all significantly lower plasma triglyceride levels, with pGlu($Lys^8$GluPAL)apelin-13-amide appearing to be the most effective. pGlu($Lys^8$GluPAL)apelin-13-amide is the only peptide tested to significantly lower total cholesterol levels in plasma (FIG. 34). ($Lys^8$GluPAL)apelin-13-amide and pGlu(Lys8GluPAL)apelin-13-amide both significantly lowered LDL-cholesterol levels compared to the high fat fed controls, similar to the lean control mice fed a normal diet. ($Lys^8$GluPAL)apelin-13-amide and pGlu(Lys8GluPAL)apelin-13-amide also both significantly increased HDL-cholesterol levels compared to the lean control and high fat fed mice.

REFERENCES

Boucher J, Masri B, Daviaud D, Gesta S, Guigne C, Mazzucotelli A, Castan-Laurell I, Tack I, Knibiehler B, Carpene C, Audigier Y, Saulnier-Blache J S & Valet P (2005) Apelin, a newly identified adipokine up-regulated by insulin and obesity. *Endocrinology* 146 1764-71.

Castan-Laurell I, Vitkova M, Daviaud D, Dray C, Kovacikova M, Kovacova Z, Hejnova J, Stich V & Valet P 2008 Effect of hypocaloric diet-induced weight loss in obese women on plasma apelin and adipose tissue expression of apelin and APJ. *European Journal of Endocrinology* 158 905-10.

Cheng B, Chen J, Bai B & Xin Q 2012 Neuroprotection of apelin and its signalling pathway. *Peptides* 37 171-173.

Chun H J, Ali Z A, Kojima Y, Kundu R K, Sheikh A Y, Agrawal R, Zheng L, Leeper N J, Pearl N E, Patterson A J, Anderson J P, Tsao P S, Lenardo M J, Ashley E A & Quertermous T 2008 Apelin signalling antagonizes Ang II effects in mouse models of atherosclerosis. *Journal of Clinical Investigation* 118 3343-3354.

Dray C, Knauf C, Daviaud D, Waget A, Boucher J, Buléon M, Cani P D, Attané C, Guigné C, Carpéné C, Burcelin R, Castan-Laurell I & Valet P 2008 Apelin stimulates glucose utilization in normal and obese insulin-resistant mice. *Cell Metabolism* 8 437-45.

El Messari S, Iturrioz X, Fassot C, De Mota N, Roesch D & Llorens-Cortes C 2004 Functional dissociation of apelin receptor signaling and endocytosis: implications for the effects of apelin on arterial blood pressure. *Journal of Neurochemistry* 90 1290-301.

Gault V A, McClean P L, Cassidy R S, Irwin N & Flatt P R 2007 Chemical gastric inhibitory polypeptide receptor antagonism protects against obesity, insulin resistance, glucose intolerance and associated disturbances in mice fed high-fat and cafeteria diets. *Diabetologia* 50 1752-1762.

Higuchi K, Masaki T, Gotoh K, Chiba S, Katsuragi I, Tanaka K, Kakuma T & Yoshimatsu H 2007 Apelin, an APJ receptor ligand, regulates body adiposity and favours the messenger ribonucleic acid expression of uncoupling proteins in mice. *Endocrinology* 148 2690-7.

Kidoya H & Takakura N 2012 Biology of the apelin-APJ axis in vascular formation. *Journal of Biochemistry* 152 125-131.

Kawamata Y, Habata Y, Fukusumi S, Hosoya M, Fujii R, Himuma S, Nishizawa N, Kitada C, Onda H, Nishimura O & Fujino M 2001 Molecular properties of apelin: tissue distribution and receptor binding. *Biochimica et Biophysica Acta* 23 162-71.

Lee D K, Saldivia V R, Nguyen T, Cheng R, George S R & O'Dowd B F 2005 Modification of the terminal residue of apelin-13 antagonizes its hypotensive action. *Endocrinology* 146 231-236.

Liu Q F, Yu H W, You L, Liu M X, Li K Y & Tao G Z 2013 Apelin-13-induced proliferation and migration induced of rat vascular smooth muscle cells is mediated by the upregulation of Egr-1. *Biochemical and Biophysical Research Communications* doi: 10.1016/j.bbrc.2013.08.051

Mitra A, Katovich, M J, Mecca A, Rowland N E 2006 Effects of central and peripheral injections of apelin on fluid intake and cardiovascular parameters in rats. *Physiology & Behaviour* 89 221-225.

O'Shea M, Hansen M J, Tatemoto K & Morris M J 2003 Inhibitory effect of apelin-12 on nocturnal food intake in the rat. Nutritional *Neuroscience* 3 163-7

Pitkin S L, Maguire J J, Bonner T I & Davenport A P 2010 International Union of Basic and Clinical Pharmacology. LXXIV. Apelin receptor nomenclature, distribution, pharmacology, and function. *Pharmacological Reviews* 62 331-42.

Quazi R, Palaniswamy C & Frishman W H 2009 The emerging role of apelin in cardiovascular disease and health. *Cardiology Reviews.* 17 283-286.

Ringström C, Nitert M D, Bennet H, Fex M, Valet P, Rehfeld J F, Friis-Hansen L & Wierup N 2010 Apelin is a novel islet peptide. *Regulatory Peptides* 162 44-51.

Sörhede Winzell M, Magnusson C & Ahren B 2005 The APJ receptor is expressed in pancreatic islets and its ligand, apelin, inhibits insulin secretion in mice. *Regulatory Peptides* 131 12-17.

Sunter D, Hewson A K & Dickson S L 2003 Intracerebroventricular injection of apelin-13 reduces food intake in the rat. *Neuroscience Letters* 353 1-4.

Tatemoto K, Hosoya M, Habata Y, Fujii R, Kakegawa T, Zou M X, Kawamata Y, Fukusumi S, Hinuma S, Kitada C, Kurokawa T, Onda H & Fujino M 1998 Isolation and characterization of a novel endogenous peptide ligand for the human APJ receptor. *Biochemical and Biophysical Research Communications* 251 471-6.

Valle A, Hoggard N, Adams A C, Roca P & Speakman J R 2008 Chronic central administration of apelin-13 over 10 days increases food intake, body weight, locomotor activity and body temperature in C57BL/6 mice. *Journal of Neuroendocrinology* 20 9-84.

Vickers C, Hales P, Kaushik V, Dick L, Gavin J, Tang J, Godbout K, Parsons T, Baronas E, Hsieh F, Acton S, Patane M, Nichols A & Tummino P 2002 Hydrolysis of biological peptides by human angiotensin-converting enzyme-related carboxypeptidase. *The Journal of Biological Chemistry* 277 14838-43.

Xu S, Han P, Huang M, Wu J C, Chang C, Tsao P S & Yue P 2010 In vivo, ex vivo, and in vitro studies on apelin's effect on myocardial glucose uptake. *Peptides* 37 320-6.

Yue P, Jin H, Aillaud M, Deng A C, Azuma J, Asagami T, Kundu R K, Reaven G M, Quertermous T & Tsao P S 2010 Apelin is necessary for the maintenance of insulin sensitivity. *American Journal of Physiology, Endocrinology and Metabolism* 298 59-6.

Zhu S, Sun F, Li W, Cao Y, Wang C, Wang Y, Liang D, Zhang R, Zhang S, Wang H, Cao F 2011 Apelin stimulates glucose uptake through the PI3K/Akt pathway and improves insulin resistance in 3T3-L1 adipocytes. *Molecular and Cellular Biochemistry* 353 303-313.

The invention is not limited to the embodiments described herein but can be amended or modified without departing from the scope of the present invention.

---

The invention claimed is:

1. A peptide analogue comprising at least residues 2-13 of SEQ ID NO: 1 and further comprising at least one from the group consisting of a substitution and a modification at residue 13 or SEQ ID NO: 1;

those amino acids present at positions 2-7 and 9-12 of the peptide analogue are unsubstituted with respect to the corresponding residues of SEQ ID NO: 1;

an N-terminal addition with at least one from the group consisting of pGlu (5-oxoproline), an acetyl moiety, an acyl moiety, and an acylated moiety; and a modification at residue 8 of SEQ ID NO: 1.

2. The peptide analogue of claim 1, wherein the peptide analogue is at least one from the group consisting of pGlu (Tyr$^{13}$)apelin-13, (pGlu)apelin-13-amide, and, pGlu (Lys$^8$GluPAL)apelin-13-amide.

3. A pharmaceutical composition comprising the peptide analogue of claim 1 in association with a pharmaceutically acceptable excipient.

4. The peptide analogue of claim 1, wherein residue 13 is the C-terminal residue and the modification at residue 13 is the substitution of the terminal carboxyl group by an amide group.

5. A peptide analogue consisting of at least residues 2-13 of SEQ ID NO: 1, wherein residue 13 is the C-terminal residue and the terminal carboxyl group of residue 13 is replaced by an amide group; and comprising an N-terminal addition of pGlu (5-oxoproline) or an acetyl, acyl or acylated moiety; and comprising a modification at residue 8 of SEQ ID NO: 1.

6. The peptide of claim 5, wherein the modification at residue 8 is the fatty acid addition at an epsilon amino group of residue 8.

7. A peptide comprising pGlu-Arg-Pro-Arg-Leu-Ser-His-Lys(gluPAL)-Gly-Pro-Met-Pro-Phe-amide.

8. A pharmaceutical composition comprising the peptide analogue of claim 7 in association with a pharmaceutically acceptable excipient.

9. A method of treating diabetes, the method comprising administering to an individual (pGlu)apelin 13 amide or the peptide analogue of claim 1.

10. A method of stimulating insulin release, the method comprising administering to an individual (pGlu)apelin-13 amide or the peptide analogue of claim 1.

11. A method of moderating blood glucose excursions, the method comprising administering to an individual (pGlu)apelin-13 amide or the peptide analogue of claim 1.

12. A method of increasing food intake or increasing body weight, the method comprising administering to an individual (pGlu)apelin-13 amide or the peptide analogue of claim 1.

13. A method of suppressing appetite or reducing body weight, the method comprising administering to an individual (pGlu)apelin-13 amide or the peptide analogue of claim 1.

14. A method of reducing blood pressure, the method comprising administering to an individual (pGlu)apelin-13 amide or the peptide analogue of claim 1.

* * * * *

SEQUENCE LISTING

<160> NUMBER OF SEQ ID NOS: 10

<210> SEQ ID NO 1
<211> LENGTH: 13
<212> TYPE: PRT
<213> ORGANISM: Homo sapiens

<400> SEQUENCE: 1

Gln Arg Pro Arg Leu Ser His Lys Gly Pro Met Pro Phe
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Analogue of apelin-13

<400> SEQUENCE: 2

-continued

```
Gln Arg Pro Arg Leu Ser His Lys Gly Pro Met Pro Ala
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Analogue of apelin-13

<400> SEQUENCE: 3

Gln Arg Pro Arg Leu Ser His Lys Gly Pro Met Pro Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Analogue of apelin-13

<400> SEQUENCE: 4

Gln Arg Pro Arg Leu Ser His Lys Gly Pro Met Pro Tyr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (13)..(13)
<223> OTHER INFORMATION: AMIDATION

<400> SEQUENCE: 5

Gln Arg Pro Arg Leu Ser His Lys Gly Pro Met Pro Phe
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (1)..(1)
<223> OTHER INFORMATION: Residue is modified to pyroglutamic acid (pGlu)

<400> SEQUENCE: 6

Glu Arg Pro Arg Leu Ser His Lys Gly Pro Met Pro Phe
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (1)..(1)
<223> OTHER INFORMATION: Residue is modified to pyroglutamic acid (pGlu)

<400> SEQUENCE: 7

Glu Arg Pro Arg Leu Ser His Lys Gly Pro Met Pro Ala
```

```
                        -continued
1               5                  10

<210> SEQ ID NO 8
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (1)..(1)
<223> OTHER INFORMATION: Residue is modified to pyroglutamic acid (pGlu)

<400> SEQUENCE: 8

Glu Arg Pro Arg Leu Ser His Lys Gly Pro Met Pro Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (1)..(1)
<223> OTHER INFORMATION: Residue is modified to pyroglutamic acid (pGlu)

<400> SEQUENCE: 9

Glu Arg Pro Arg Leu Ser His Lys Gly Pro Met Pro Tyr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Analogue of apelin-13
<220> FEATURE:
<221> NAME/KEY: MOD_RES
<222> LOCATION: (1)..(1)
<223> OTHER INFORMATION: Residue is modified to pyroglutamic acid (pGlu)
<220> FEATURE:
<221> NAME/KEY: MOD_RES
<222> LOCATION: (13)..(13)
<223> OTHER INFORMATION: AMIDATION

<400> SEQUENCE: 10

Glu Arg Pro Arg Leu Ser His Lys Gly Pro Met Pro Phe
1               5                   10
```